United States Patent
Roberts et al.

(10) Patent No.: US 6,713,248 B2
(45) Date of Patent: Mar. 30, 2004

(54) METHODS FOR DETECTION OF GAMMA-SECRETASE ACTIVITY AND IDENTIFICATION OF INHIBITORS THEREOF

(75) Inventors: Susan B. Roberts, Madison, CT (US); Roger Hochoon Pak, Southington, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/823,153

(22) Filed: Mar. 30, 2001

(65) Prior Publication Data

US 2002/0025540 A1 Feb. 28, 2002

Related U.S. Application Data

(60) Provisional application No. 60/194,495, filed on Apr. 3, 2000.

(51) Int. Cl.$^7$ ............... C12Q 1/00; G01N 33/53; G01N 33/542

(52) U.S. Cl. ............... 435/4; 435/7.9; 435/7.92

(58) Field of Search ............ 435/7.9, 23, 226, 435/6, 7.21, 4, 69.1, 325; 530/391.1, 329, 300, 350, 7.92

(56) References Cited

U.S. PATENT DOCUMENTS

| | | | |
|---|---|---|---|
| 4,956,274 A | * 9/1990 | Khanna et al. | 435/7 |
| 5,703,129 A | 12/1997 | Felsenstein et al. | |
| 5,744,346 A | 4/1998 | Chrysler et al. | |
| 5,837,838 A | 11/1998 | Reed et al. | |
| 5,840,540 A | 11/1998 | St. George-Hyslop et al. | |
| 5,876,946 A | * 3/1999 | Burbaum et al. | 435/7.1 |
| 5,877,399 A | 3/1999 | Hsiao et al. | |
| 5,894,078 A | 4/1999 | Nalbantoglu et al. | |
| 5,898,094 A | 4/1999 | Duff et al. | |
| 5,928,882 A | 7/1999 | Sabo et al. | |
| 5,942,400 A | 8/1999 | Anderson et al. | |
| 5,945,330 A | 8/1999 | Hillman et al. | |
| 5,976,817 A | 11/1999 | Davies-Heerema et al. | |
| 5,986,054 A | 11/1999 | St. George-Hyslop et al. | |
| 6,245,884 B1 | * 6/2001 | Hook | 530/300 |
| 6,579,689 B2 | * 6/2003 | Coredell et al. | 435/7.92 |
| 2001/0034884 A1 | 10/2001 | Peraus | 800/3 |
| 2001/0055782 A1 | * 12/2001 | Cordell et al. | 435/7.92 |
| 2002/0015941 A1 | * 2/2002 | Kim et al. | 435/4 |
| 2002/0025508 A1 | * 2/2002 | Fechteler et al. | 435/4 |
| 2003/0022251 A1 | * 1/2003 | Fuchs et al. | 435/7.21 |

FOREIGN PATENT DOCUMENTS

| | | | |
|---|---|---|---|
| CA | 2381952 | 3/2001 | |
| WO | WO98/15828 | 4/1998 | |
| WO | WO 00/03248 | * 1/2000 | G01N/33/68 |
| WO | WO00/42166 | 7/2000 | |
| WO | WO2001/16355 | 3/2001 | |

OTHER PUBLICATIONS

Kimberly et al. (Feb. 4, 2000) The Transmembrane Aspartates in Presenilin 1 and 2 are Obligatory for g–secretase Activity and Amyloid b–Protein Generation. The Journal of Biological Chemistry 275(4): 3173–3178.*
Mundy, Biochemical and Biophysical Research Communications, 204:333–341.
Kang et al., 1987, Nature, vol. 325, 733–736.
Levy–Lehad et al., 1995, Science, vol. 269, 973–977.
Lammich et al., 1999, PNAS, vol. 96, No. 7, 3922–3927.
Dovey et al., 1993, Neuroreport, vol. 4, No. 8, 1039–1042.
Selkoe, 1994, Ann. Rev. Cell Biol., vol. 10, 373–403.
Asami–Odaka et al., 1995, Biochemistry, vol. 34, No. 32, 10272–10278.
Joachim et al., 1988, Brain Research, vol. 474, 100–111.
Castano et al., 1988, Laboratory Investigation, vol. 58, No. 2, 122–132.
Roher et al., 1993, PNAS, vol. 90, 10836–10840.
Iwatsubo et al., 1994, Neuron, vol. 13, 45–53.
Yamaguchi et al., 1995, Amyloid: Int. J. Clin. Invest., vol. 2, 7–16.
Mann et al., 1996, American Journal of Pathology, vol. 148, No. 4, 1257–1266.
Durkin et al., 1999, Journal of Biol. Chem., vol. 274, No. 29, 20499–20504.
Seubert et al., 1992, Nature, vol. 359, 325–327.
Shoji et al., 1992, Science, vol. 258, 126–129.
Scheuener et al., 1996, Nature Medicine, vol. 2, No. 8, 864–870.
Duff et al., 1996, Nature, vol. 383, 710–713.
Borchelt et al., 1996, Neuron, vol. 17, 1005–1013.

(List continued on next page.)

*Primary Examiner*—Elizabeth Kemmerer
*Assistant Examiner*—Christopher James Nichols
(74) *Attorney, Agent, or Firm*—John A. Lamerdin; Briana Buchholz

(57) ABSTRACT

The present invention provides an isolated, functionally-active protein that catalyzes cleavage of a gamma-secretase substrate. The functional activity of the isolated protein suggests that the isolated protein includes gamma-secretase. In one embodiment, the isolated gamma-secretase protein is associated with PS1. The present invention also relates to homogeneous methods for monitoring cleavage of β-amyloid precursor protein (βAPP) by gamma-secretase, wherein the steps of of isolating and retrieving cleavage products have been eliminated. Cleavage can be detected by binding a pair of fluorescent adducts to the gamma-cleaved βAPP fragment. Preferably, a first fluorescent adduct binds to the carboxy-terminal end of the gamma-cleaved βAPP fragment, with substantially no cross-reactivity to uncleaved βAPP or to other types of gamma-cleaved βAPP fragments, while a second fluorescent adduct binds to a portion within the amino-terminal region on the gamma-cleaved βAPP fragment. Detection of binding to the gamma-cleaved βAPP fragment is determined by monitoring the fluorescent energy transfer between the adducts.

54 Claims, 14 Drawing Sheets

OTHER PUBLICATIONS

Citron et al., 1997, Nature Medicine, vol. 3, No. 1, 67–72.
Goate et al., 1991, Nature, vol. 349, 704–706.
Chartier–Harlin et al., 1991, Nature, vol. 353, 844–846.
Murrell et al., 1991, Science, vol. 254, 97–99.
Karlinsky et al., 1992, Neurology, vol. 42, 1445–1453.
Mullan et al., 1992, Nature Genetics, vol. 1, 345–347.
Rogaev et al., 1995, Nature, vol. 376, 775–778.
Doan et al., 1996, Neuron, vol. 17, 1023–1030.
Xia et al., 1998, Biochemistry, vol. 37, No. 47. 16465–16471.
Kovacs et al., 1996, Nature Medicine, vol. 2, No. 2, 224–229.
Ray et al., 1999, J. Biol. Chem., 274, Issue 51, 36801–36807.
Hua et al., 1996, Cell, vol. 87, 415–426.
Brown et al., 1997, Cell, vol. 89, 331–340.
Artavanis–Tsakonas et al., 1996, Sciece, vol. 268, 225–232.
Kopan et al., 1996, Current Opinion in Neurobiology, vol. 6, 594–601.
Weinmaster 1997 Mol. Cell Neuroscience, vol. 9, 91–102.
Schroeter et al., 1998, Nature, 393, 382–386.
Selkoe, 1999, Nature, vol. 399, Supp., A23–A31.
Brown et al., 2000, Cell, vol. 100, 391–398.
Mumm et al., 2000, Molecular Cell, vol. 5, 197–206.
Seiffert et al., 2000, J. Biol. Chem., vol. 275, No. 44, 34086–34091.
Herreman et al., 2000, Nature Cell Biology, vol. 2, 461–462.
Esler et al., 2000, Nature cell Biology, vol. 2, 428–434.
Li et al., 2000, Nature, 405, 689–694.
Li et al., 2000, PNAS, vol. 97, No. 11, 6138–6143.
Sherrington et al., 1995, Nature, vol. 375, 754–760.
Haas et al., 1993, Cell, vol. 75, 1039–1042.
Tomita et al., 1997, Proc. Natl Acad. Sci., vol. 94, 2025–2030.
Citron et al., 1996, Proc. Natl. Acad. Sci., vol. 93, 13170–13175.
Klafki et al., 1996, J. Biol. Chem., vol. 271, No. 45, 28655–28659.
DeStoooper et al., 1998, Nature, 391, No. 6665, 387–390.
Wolfe et al., 1999, Nature, 398, 513–517.
Wolfe et al., 1999, Biochemistry, 38, 4720–4727.
Vassar et al., 1999, Science, vol. 286, 735–741.
Sakai et al., 1997, J. Biol. Chem., vol. 272, No. 32, 20213–20221.
Rawson et al., 1997, Molecular Cell, vol. 1, 47–57.
Wasco et al., 1992, PNAS, vol. 89, 10758–10762.
Naruse et al.,1998, Neuron, vol. 21, 1213–1221.
Haass, 1997, Neuron, vol. 18, 687–690.
Pinnix et al., 2001, J. Biol. Chem., vol. 276, 481–487.
Mclendon et al., 2000, The FASEB Journal, 14, 2383–2386.
Yu et al., 2000, Nature, 407, 48–54.
Shearman et al., 2000, Biochemistry, vol. 39, 8698–8704.
Brennan, 2000, Chemical & Engineering News, 56–58.
Clarke et al., 2000, Journal of Neuroscience Methods, 102, 61–68.
Hardy, 1997, PNAS, vol. 94, 2095–2097.
Higaki et al., 1995, vol. 14, 651–659.
Octave et al., 2000, Journal of Biological Chemistry, vol. 275, No. 3, 1525–1528.
Selkoe, 1996, Journal of Biological Chemistry, vol. 271, No. 31, 18295–18298.
Skovronsky et al., 2000, Chemistry, vol. 39, 810–817.
St George–Hyslop et al., 1999, Nature, vol. 400, 116–117.
Steiner et al., 1999, FEBS Letters, vol. 463, No. 3, 245–249.
Zhang et al., 2000, Nature Cell Biology, vol. 2, 463–465.
Strooper, 2000, Nature, vol. 405, 627–628.
Leonhard et al., 1996, The EMBO Journal, vol. 15, No. 16, 4218–4229.
Artvanis–Tsakonas et al., 1995, Science, vol. 268, 225–232.
Irvine, 1999, Current Opinion in Genetics & Development, 9, 434–441.
Duncan et al., 1997, The Journal of Biological Chemistry, vol. 272, No. 19, 12778–12785.
Boyartchuk et al., 1997, Science, vol. 275, 1796–1800.
Duffy et al., 1996, Current Opinion in Cell Biology, vol. 8, 231–238.

* cited by examiner

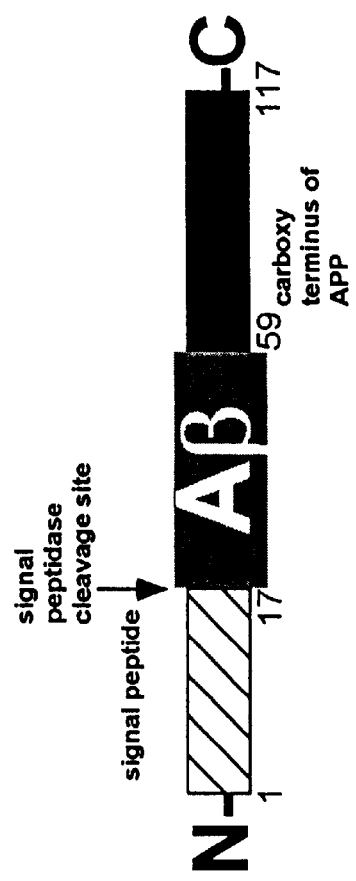
Figure 1a: Schematic of recombinant vector that encodes the human βAPP-C100.

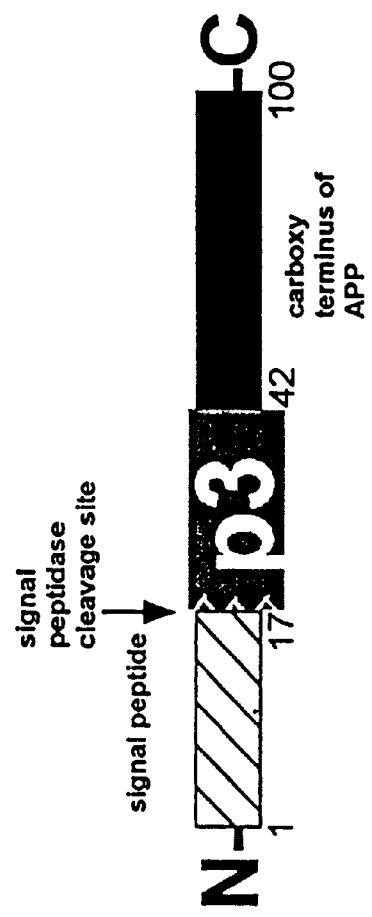
Figure 1b: Schematic of the recombinant vector that encodes the human βAPP-C83 polypeptide.

Figure 2: The nucleotide and amino acid sequence of the recombinant βAPP (C-100) polypeptide substrate.

```
            10              20              30              40              50
            .               .               .               .               .
     ATGCTGCCCGGTTTGGCACTGTTCCTGCTGGCCGCCTGGACGGCTCGGGCGCTGGATGCA
   1  M  L  P  G  L  A  L  F  L  L  A  A  W  T  A  R  A  L  D  A   20

70              90              110
            .               .               .
     GAATTCCGACATGACTCAGGATATGAAGTTCATCATCAAAAATTGGTGTTCTTTGCAGAA
  21  E  F  R  H  D  S  G  Y  E  V  H  H  Q  K  L  V  F  F  A  E   40

130             150             170
            .               .               .
     GATGTGGGTTCAAACAAAGGTGCAATCATTGGACTCATGGTGGGCGGTGTTGTCATAGCG
  41  D  V  G  S  N  K  G  A  I  I  G  L  M  V  G  G  V  V  I  A   60

190             210             230
            .               .               .
     ACAGTGATCGTCATCACCTTGGTGATGCTGAAGAAGAAACAGTACACATCCATTCATCAT
  61  T  V  I  V  I  T  L  V  M  L  K  K  K  Q  Y  T  S  I  H  H   80

250             270             290
            .               .               .
     GGTGTGGTGGAGGTTGACGCCGCTGTCACCCCAGAGGAGCGCCACCTGTCCAAGATGCAG
  81  G  V  V  E  V  D  A  A  V  T  P  E  E  R  H  L  S  K  M  Q   100

310             330             350
            .               .               .
     CAGAACGGCTACGAAAATCCAACCTACAAGTTCTTTGAGCAGATGCAGAACTAG
 101  Q  N  G  Y  E  N  P  T  Y  K  F  F  E  Q  M  Q  N  *   118
```

Figure 3: The nucleotide and amino acid sequence of the recombinant βAPP (C-83) polypeptide substrate.

```
                       10                  20                  30                  40                  50
                       .                   .                   .                   .                   .
      ATGCTGCCCGGTTTGGCACTGTTCCTGCTGGCCGCCGCCTGGACGGCTCGGGCGCTGGATGCA
  1    M   L   P   G   L   A   L   F   L   L   A   A   A   W   T   A   R   A   L   D   A      20

70                  90                 110
                       .                   .                   .
      GAATTCGTCGTTCTTTGCAGAAGATGTGGGTTCAAACAAAGGTGCAATCATTGGACTCATG
 21    E   F   V   F   F   A   E   D   V   G   S   N   K   G   A   I   I   G   L   M       40

130                 150                 170
                       .                   .                   .
      GTGGGCGGTGTTGTCATAGCGACAGTGATCGTCATCACCTTGGTGATGCTGAAGAAGAAA
 41    V   G   G   V   V   I   A   T   V   I   V   I   T   L   V   M   L   K   K   K       60

190                 210                 230
                       .                   .                   .
      CAGTACACACATCCATTCATCATGGTGTGGTGGAGGTTGACGCCGCTGTCACCCCAGAGGAG
 61    Q   Y   T   S   I   H   H   G   V   V   E   V   D   A   A   V   T   P   E   E       80

250                 270                 290
                       .                   .                   .
      CGCCACCTGTCCAAGATGCAGCAGAACGGCTACGAAAATCCAACTACAAGTTCTTTGAG
 81    R   H   L   S   K   M   Q   Q   N   G   Y   E   N   P   T   Y   K   F   F   E      100

310
                       .
      CAGATGCAGAACTAG
101    Q   M   Q   N   *     105
```

Figure 4: Gamma-secretase cleavage sequence within a Beta-secretase cleaved human βAPP fragment.

```
1                                16                                38   40 4243        49
DAEFGHDSGFEVRHQKLVFFAEDVGSNKGAIIGLMVGG^VVIA^T^VIVITL^VMLKKK
```

Figure 5: Putative gamma-secretase cleavage sequence within an S2-cleaved human Notch-1 fragment.

VQSETVEPPPPAQLHFMYVAAAAFVLLFFVGCGVLLSRKRR

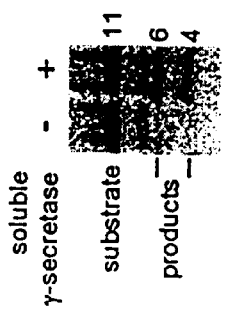
Figure 6: cleavage of 35S-C100 by soluble gamma secretase preparation.

Figure 7: cleavage of 35S-C83 and -C100 by soluble gamma secretase preparation.
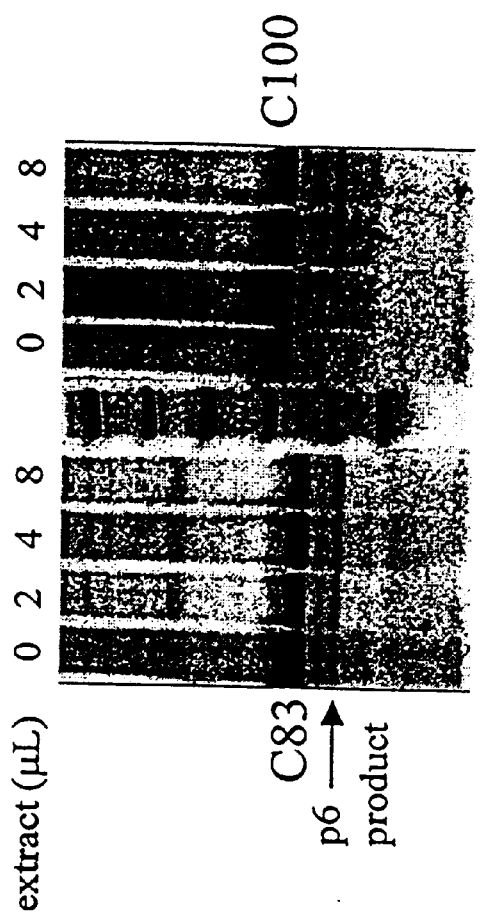

Figure 8: cleavage of 35S-C100 by immunoisolated gamma secretase preparation
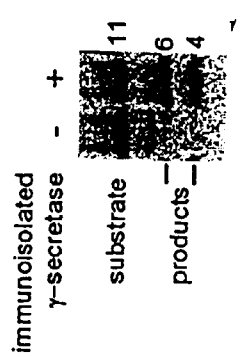

Fluorescent Donor Molecules
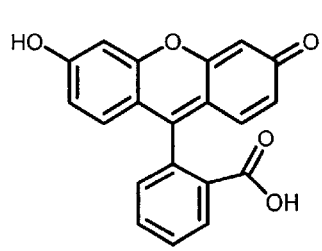
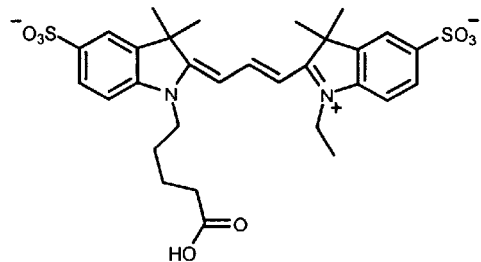
Fluorescein                Cy3
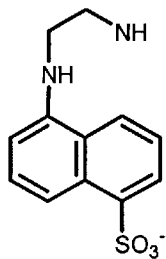
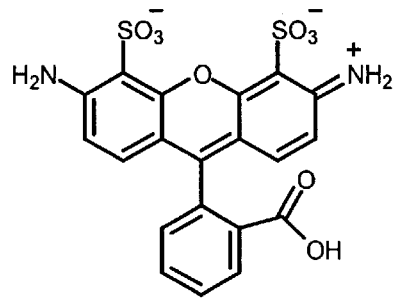
EDANS                      Alexa Fluor
FIGURE 12

Fluorescent Acceptor Molecules
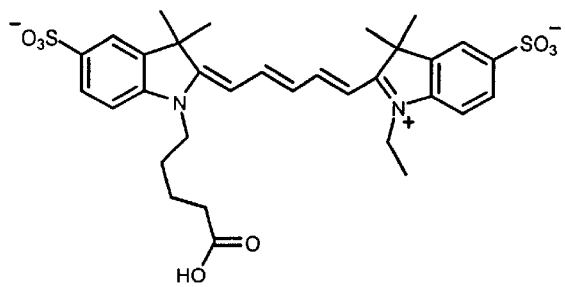
Cy5
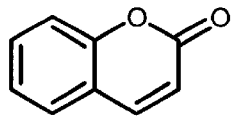
Coumarin
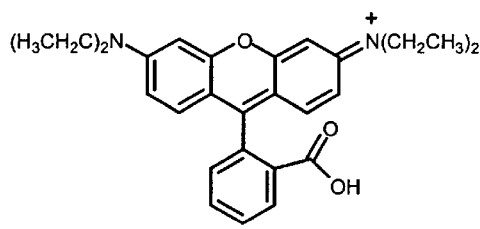
Rhodamine
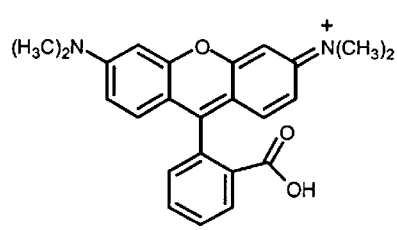
Tetramethylrhodamine
Fluorescent Acceptor Molecules which may act as Quenchers
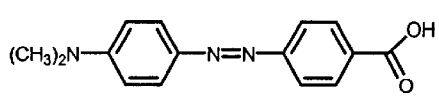
Dabcyl
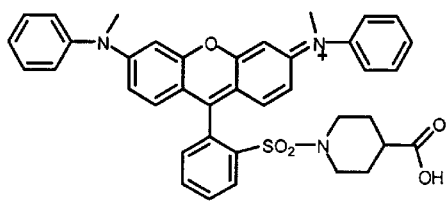
QSY-7
FIGURE 13

SEQUENCE LISTING

<160> NUMBER OF SEQ ID NOS: 11

<210> SEQ ID NO 1
<211> LENGTH: 354
<212> TYPE: DNA
<213> ORGANISM: Human Beta App

<400> SEQUENCE: 1

| | | | | | |
|---|---|---|---|---|---|
| atgctgcccg | gtttggcact | gttcctgctg | gccgcctgga | cggctcgggc | gctggatgca | 60 |
| gaattccgac | atgactcagg | atatgaagtt | catcatcaaa | aattggtgtt | ctttgcagaa | 120 |
| gatgtgggtt | caaacaaagg | tgcaatcatt | ggactcatgg | tgggcggtgt | tgtcatagcg | 180 |
| acagtgatcg | tcatcacctt | ggtgatgctg | aagaagaaac | agtacacatc | cattcatcat | 240 |
| ggtgtggtgg | aggttgacgc | cgctgtcacc | ccagaggagc | gccacctgtc | caagatgcag | 300 |
| cagaacggct | acgaaaatcc | aacctacaag | ttctttgagc | agatgcagaa | ctag | 354 |

<210> SEQ ID NO 2
<211> LENGTH: 117
<212> TYPE: PRT
<213> ORGANISM: Human Beta App

<400> SEQUENCE: 2

Met Leu Pro Gly Leu Ala Leu Phe Leu Leu Ala Ala Trp Thr Ala Arg
1               5                   10                  15

```
Ala Leu Asp Ala Glu Phe Arg His Asp Ser Gly Tyr Glu Val His His
            20                  25                  30

Gln Lys Leu Val Phe Phe Ala Glu Asp Val Gly Ser Asn Lys Gly Ala
        35                  40                  45

Ile Ile Gly Leu Met Val Gly Gly Val Val Ile Ala Thr Val Ile Val
 50                  55                  60

Ile Thr Leu Val Met Leu Lys Lys Lys Gln Tyr Thr Ser Ile His His
 65                  70                  75                  80

Gly Val Val Glu Val Asp Ala Ala Val Thr Pro Glu Glu Arg His Leu
                85                  90                  95

Ser Lys Met Gln Gln Asn Gly Tyr Glu Asn Pro Thr Tyr Lys Phe Phe
            100                 105                 110

Glu Gln Met Gln Asn
        115

<210> SEQ ID NO 3
<211> LENGTH: 315
<212> TYPE: DNA
<213> ORGANISM: Human Beta App

<400> SEQUENCE: 3
atgctgcccg gtttggcact gttcctgctg gccgcctgga cggctcgggc gctggatgca      60
gaattcgtgt tctttgcaga agatgtgggt tcaaacaaag gtgcaatcat tggactcatg     120
gtgggcggtg ttgtcatagc gacagtgatc gtcatcacct tggtgatgct gaagaagaaa     180
cagtacacat ccattcatca tggtgtggtg gaggttgacg ccgctgtcac cccagaggag     240
cgccacctgt ccaagatgca gcagaacggc tacgaaaatc caacctacaa gttctttgag     300
cagatgcaga actag                                                      315

<210> SEQ ID NO 4
<211> LENGTH: 104
<212> TYPE: PRT
<213> ORGANISM: Human Beta App

<400> SEQUENCE: 4

Met Leu Pro Gly Leu Ala Leu Phe Leu Leu Ala Ala Trp Thr Ala Arg
 1               5                  10                  15

Ala Leu Asp Ala Glu Phe Val Phe Ala Glu Asp Val Gly Ser Asn
            20                  25                  30

Lys Gly Ala Ile Ile Gly Leu Met Val Gly Gly Val Val Ile Ala Thr
        35                  40                  45

Val Ile Val Ile Thr Leu Val Met Leu Lys Lys Lys Gln Tyr Thr Ser
 50                  55                  60

Ile His His Gly Val Val Glu Val Asp Ala Ala Val Thr Pro Glu Glu
 65                  70                  75                  80

Arg His Leu Ser Lys Met Gln Gln Asn Gly Tyr Glu Asn Pro Thr Tyr
                85                  90                  95

Lys Phe Phe Glu Gln Met Gln Asn
            100

<210> SEQ ID NO 5
<211> LENGTH: 16
<212> TYPE: PRT
<213> ORGANISM: Artificial Sequence
<220> FEATURE:
<221> NAME/KEY: misc_feature
<223> OTHER INFORMATION: Description of Artificial Sequence: PS1
      PEPTIDE
```

```
<400> SEQUENCE: 5

Cys Arg Asp Ser His Leu Gly Pro His Arg Ser Thr Pro Glu Ser Arg
1               5                   10                  15

<210> SEQ ID NO 6
<211> LENGTH: 17
<212> TYPE: PRT
<213> ORGANISM: Artificial Sequence
<220> FEATURE:
<221> NAME/KEY: misc_feature
<223> OTHER INFORMATION: Description of Artificial Sequence:  PS1
      PEPTIDE

<400> SEQUENCE: 6

Cys Gly His Pro Glu Pro Leu Ser Asn Gly Arg Pro Gln Gly Asn Ser
1               5                   10                  15

Arg

<210> SEQ ID NO 7
<211> LENGTH: 239
<212> TYPE: PRT
<213> ORGANISM: Artificial Sequence
<220> FEATURE:
<221> NAME/KEY: misc_feature
<223> OTHER INFORMATION: Description of Artificial Sequence:  PS1
      PEPTIDE

<400> SEQUENCE: 7

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Glu Phe Pro Gly Arg Leu Glu Arg Pro His Arg Asp
225                 230                 235
```

<210> SEQ ID NO 8
<211> LENGTH: 354
<212> TYPE: PRT
<213> ORGANISM: Artificial Sequence
<220> FEATURE:
<221> NAME/KEY: misc_feature
<223> OTHER INFORMATION: Description of Artificial Sequence: PS1 PEPTIDE

<400> SEQUENCE: 8

```
Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
210                 215                 220

Gly Ser Leu Phe Pro Ala Leu Ile Tyr Ser Ser Thr Met Val Trp Leu
225                 230                 235                 240

Val Asn Met Ala Glu Gly Asp Pro Glu Ala Gln Arg Arg Val Ser Lys
                245                 250                 255

Asn Ser Lys Tyr Asn Ala Glu Ser Thr Glu Arg Glu Ser Gln Asp Thr
            260                 265                 270

Val Ala Glu Asn Asp Asp Gly Gly Phe Ser Glu Glu Trp Glu Ala Gln
275                 280                 285

Arg Asp Ser His Leu Gly Pro His Arg Ser Thr Pro Glu Ser Arg Ala
            290                 295                 300

Ala Val Gln Glu Leu Ser Ser Ser Ile Leu Ala Gly Glu Asp Pro Glu
305                 310                 315                 320

Glu Arg Gly Val Lys Leu Gly Leu Gly Asp Phe Ile Phe Tyr Ser Val
                325                 330                 335

Leu Val Gly Lys Ala Ser Ala Thr Ala Ser Gly Asp Trp Asn Thr Thr
            340                 345                 350
```

```
Ile Ala

<210> SEQ ID NO 9
<211> LENGTH: 15
<212> TYPE: PRT
<213> ORGANISM: Artificial Sequence
<220> FEATURE:
<221> NAME/KEY: misc_feature
<223> OTHER INFORMATION: Description of Artificial Sequence:  PS1
      PEPTIDE

<400> SEQUENCE: 9

Arg Asp Ser His Leu Gly Pro His Arg Ser Thr Pro Glu Ser Arg
1               5                   10                  15

<210> SEQ ID NO 10
<211> LENGTH: 55
<212> TYPE: PRT
<213> ORGANISM: Human Beta App Fragment

<400> SEQUENCE: 10

Asp Ala Glu Phe Gly His Asp Ser Gly Phe Glu Val Arg His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr Val Ile Val Ile Thr
        35                  40                  45

Leu Val Met Leu Lys Lys Lys
        50                  55

<210> SEQ ID NO 11
<211> LENGTH: 41
<212> TYPE: PRT
<213> ORGANISM: Human Notch-1 Fragment

<400> SEQUENCE: 11

Val Gln Ser Glu Thr Val Glu Pro Pro Pro Pro Ala Gln Leu His Phe
1               5                   10                  15

Met Tyr Val Ala Ala Ala Phe Val Leu Leu Phe Phe Val Gly Cys
            20                  25                  30

Gly Val Leu Leu Ser Arg Lys Arg Arg
        35                  40
```

METHODS FOR DETECTION OF GAMMA-SECRETASE ACTIVITY AND IDENTIFICATION OF INHIBITORS THEREOF

This application claims the benefit of U.S. Provisional Patent Application No. 60/194,495, filed Apr. 3, 2000. Now Abandoned Throughout this application various publications are referenced. The disclosures of these publications in their entireties are hereby incorporated by reference into this application in order to more fully describe the state of the art to which this invention pertains.

FIELD OF THE INVENTION

The present invention relates generally to the field of plaque amyloid deposits that are the hallmarks of Alzheimer's disease. In particular, the invention relates to an isolated, functionally-active protein that has gamma-secretase activity. Gamma-secretase activity is necessary for amyloid production. The present invention also relates to methods for isolating integral-membrane proteins and protein complexes, including the gamma-secretase protein of the invention, and assays for detecting gamma-secretase activity.

BACKGROUND OF THE INVENTION

Alzheimer's disease is characterized by neuropathological lesions in the brain, marked by extracellular amyloid plaques in the cerebral and limbic cortices and intraneuronal paired helical filaments and neurofibrillary tangles. Commonly, Alzheimer's disease is a disease of the elderly with incidence increasing sharply after 60 years of age. However, early onset of Alzheimer's disease may strike patients only 40–50 years old, and is often associated with Familial Alzheimer's disease (FAD).

The course of both types of Alzheimer's disease appears to be the same. The major proteinaceous component of vascular and plaque amyloid deposits is the Aβ-42 peptide which is generated by proteolytic cleavage of βAPP. There is extensive evidence that supports the hypothesis that the Aβ-42 peptide plays an essential role in the pathogenesis of Alzheimer's disease. The generation of Aβ peptides from the β amyloid precursor protein (βAPP) involves three different protease activities designated alpha-, beta-, and gamma-secretases, and is altered by mutations in βAPP, and two different presenilins designated PS1 and PS2. To date, nucleotide sequences have been determined for βAPP (Kang, J. et al., 1987 Nature 325:733–736), PS1 (Sherrington, R., et al., 1995 Nature 375:754–760), and PS2 (Levy-Lahad, E., et al., 1995 Science 269:973–977). A candidate nucleotide sequence that may encode the protein having beta-secretase activity (Vassar, R., et al., 1999 Science 286:735–741; U.S. Pat. Nos. 5,744,346 and 5,942,400), and a candidate alpha secretase molecule (Lammich, S., et al., 1999 Proc. Natl. Acad. Sci. USA 98:3922–3927) have been identified. The isolated sequence for gamma-secretase remains elusive.

The mature βAPP protein is an integral-membrane protein found in the plasma membrane, Golgi apparatus, and endoplasmic reticulum. The βAPP protein resembles a cell-surface receptor having a large extracellular N-terminal domain, a single transmembrane domain, and a small cytoplasmic C-terminal tail (Kang, J., et al., 1987 supra). Splice variants of the βAPP mRNA encode APP polypeptides of 770, 750, and 695 amino acids. All these forms of βAPP include the cleavage region and can give rise to amyloidogenic Aβ peptides. In normal cells, βAPP undergoes one of two different sequential cleavage pathways that involve alpha-, beta-, and gamma-secretases (Dovey, H. F., et al., 1993 Neuroreport 4:1039–1042; Selkoe, D. J., et al., 1994 Ann. Rev. of Cell Biol. 10:373–403; Asami-Odaka, A., et al., 1995 Biochemistry 34:10272–10278).

In one cleavage pathway, alpha-secretase cleaves βAPP in the extracellular, membrane/proximal domain (e.g., C-terminus to amino acid residue 687 of the 770 amino acid form of βAPP) to generate a soluble N-terminal fragment (e.g., the alpha-sAPP fragment) and a membrane-bound C-terminal fragment (e.g., the 9 kDa CTF or C83 CTF). Then, gamma-secretase cleaves the membrane-bound CTF, within the membrane-bound domain, to generate the p3 fragment (e.g., the 3 kDa fragment) and a 6 kDa C-terminal fragment.

In another cleavage pathway, beta-secretase cleaves βAPP in the extracellular, membrane-proximal domain (e.g., C-terminal to amino acid residue 671 of the 770 amino acid form of βAPP) to generate a soluble N-terminal fragment (e.g., the 100 kDa NTF or beta-sAPP fragment) and a membrane-bound C-terminal fragment (e.g., the 11 kDa CTF or C 100 CTF). Then, gamma-secretase cleaves the membrane-bound CTF, within the membrane-bound domain, to generate the p6 fragment (e.g., the 6 kDa fragment) and Aβ peptide (e.g., the 4 kDa fragment).

The amino acid sequence of the gamma-secretase cleavage region is known (Duffy, C. L., et al., 1988 Brain Res. 474:100–111; Castano, E. M. and Frangione, B. 1988 Lab. Invest. 58:122–132). Gamma-secretase cleaves at variable sites within the cleavage region (Haass, C. and Selkoe, D. J. 1993 Cell 75:1039–1042) to generate a population of Aβ peptides having heterogeneous C-terminal ends. In normal patients, the Aβ peptide is found in two predominant forms, the majority Aβ-40 form and the minority Aβ-42 form each having a distinct COOH-terminus. Patients with the most common form of FAD show an increase in the amount of the 42 form. The Aβ-40 form is not associated with early deposits of amyloid plaques. In contrast, the Aβ-42 form accumulates early and predominantly in the parenchymal plaques and there is strong evidence that Aβ-42 plays a major role in amyloid plaque deposits in FAD patients (Roher, A. E., et al., 1993 Proc. Natl. Acad. Sci. USA 90:10836; Iwatasubo, T., et al., 1994 Neuron 13:45; Yamaguchi, H., et al., 1995 Amyloid Int. J. Clin. Invest. 2:7–16; Mann, D. M., et al., 1996 Am. J. Pathol. 148:1257).

It has been generally thought that the same gamma-secretase enzyme generates the –40 and –42 forms. To date, this question remains unsettled because researchers in the field have reported conflicting results. For example, two research groups have independently reported in vitro results which suggest certain protease inhibitors selectively decrease the levels of Aβ-42 and concluded that Aβ-40 and 42 are generated by two different gamma-secretases (Citron, M., et al., 1996 Proc. Nat. Acad. Sci. USA 93:13170–13175; Klafki, H. -W., et al., 1996 J. Biol. Chem. 271:28655–28659). A third research group has compared the relative ability of a series of protease inhibitors to inhibit secretion of Aβ-40 and 42 peptides and reached the opposing conclusion that the Aβ-40 and -42 peptides are generated by a single protease (Durkin, J. T. et al., 1999 Journal of Biological Chemistry 274:20499–20504).

The Aβ-40 and -42 forms are secreted constitutively in a wide variety of cells/tissues, and are found as soluble forms in biological fluids (Seubert, P., et al., 1992 Nature 359:325

375; Shoji, M., et al., 1992 *Science* 258:126–129) thus allowing extensive analysis of both forms of the Aβ peptide in FAD patients. Some FAD patients have elevated levels of the Aβ-42 peptide in their serum (Scheuner, D., et al., 1996 *Nat. Med.* 2:864–870). It is known that mutations in the βAPP, PS1 or PS2 gene, found in FAD patients, alter cleavage of the βAPP protein to increase the relative amount of the AD-42 peptide (Tomita, T. et al., 1997 *Proc. Natl. Acad. Sci. USA* 94:2025–2030; Duff, K., et al., 1996 *Nature* 383:710–713; Borchelt, D., et al., 1996 *Neuron* 17:1005–1013; Citron, M., et al., 1997 *Nat. Med.* 3:67–72).

Point mutations of the βAPP gene are linked to a relatively small number of FAD pedigrees such as βAPP-London, βAPP-Flemish, and βAPP-Swedish (Goate, A. M., et al., 1991 *Nature* 349:704–706; Chartier-Harlin, M. -C., et al., 1991 *Nature* 353:844–846; Murrell, J., et al., 1991 *Science* 254:97–99; Karlinsky, H., et al., 1992 *Neurology* 42:1445–1453; Mullan, M., et al., 1992 *Nature Genetics* 1:345–347). Point mutations of the PS2 gene are also linked to a minority of FAD cases (Levy-Lahad, E., et al., 1995 *Science* 269:973–977; Rogaev, E. I., et al., 1995 *Nature* 376:775–778). The majority of FAD cases are caused by point mutations of the PS1 gene (Sherrington, R., et al., 1995 *Nature* 375:754–760), which results in a selective increase of the Aβ-42 peptide (Scheuner, D., et al., 1996 supra).

PS1 and PS2 are integral-membrane proteins, having 6 or 8 transmembrane domains (Doan, A., et al., 1996 *Neuron* 17:1023–1030; De Stooper, B., et al., 1997 supra), and are located in the endoplasmic reticulum, early Golgi, and possibly at the cell surface (Xia, W., et al., 1998 *Biochem.* 37:16465–16471; Kovacs, D. M., et al., 1996 *Nature. Med.* 2:224–229; Ray, et al., 1999 *J. Biol. Chem.* 274:36801–36807). These presenilin proteins share 63% sequence identity.

It has been postulated that PS1 may be the elusive gamma-secretase. Evidence to support this postulate includes the observation that cells from PS1-deficient mouse embryos generate significantly reduced levels of the Aβ peptide, demonstrating that PS1 appears to play a role in facilitating gamma-secretase activity (De Stooper, B., et al., 1997 supra). In particular, it is postulated that PS1 is an autoactivated aspartyl protease having gamma-secretase activity (Wolfe, M. S., et al., 1999 *Nature* 398:513–517). This hypothesis is based on the discovery that two aspartate residues, which reside within the transmembrane domain of PS1, are required for endo-proteolytic processing of PS1 and gamma-secretase activity (Wolfe, M. S., et al., 1999 supra). Point mutations of residues aspartic acid-257 to alanine or aspartic acid-385 to alanine inhibited endo-proteolysis of PS1, and caused an accumulation of the C100 and C83 APP fragments, suggesting that these aspartate residues are required specifically for gamma-secretase activity. Similar results have been reported for mutant PS2 proteins which contain point mutations of the corresponding aspartyl residues (Kimberley, W. T., et al., 2000 *J. Biol. Chem.* 275:3173–3178). Yet there is no evidence that PS1 or PS2 directly catalyzes cleavage of a βAPP substrate. Furthermore, PS1 and PS2 lack sequences and structural similarity with known proteases and aspartyl proteases.

An alternative hypothesis suggests that PS1 functions as a regulatory cofactor of the βAPP cleavage pathway (De Stooper, B., et al., 1997 supra; Wolfe, M. S., et al., 1999 *Nature* 398:513–517). Support for this hypothesis comes from the observation that PS1 shares structural similarity with SREBP cleavage-activating protein (SCAP) which is also an integral-membrane protein having 6 to 8 transmembrane domains and plays a role in regulating cleavage of SREBP (Hua, X., et al., 1996 *Cell* 87:415–426; Brown, M. S. and Goldstein, J. L. 1997 *Cell* 89:331–340; Sakai, J., et al., 1997 *J. Biol. Chem.* 272:20213 20221).

The hypothesized roles of the presenilins and gamma-secretase are further complicated by the fact that C-terminal cleavage products of a βAPP-like protein, the APLP1 protein (Wasco, W., et al., 1992 *Proc. Natl. Acad. Sci. USA* 89:10758–10762), accumulate in primary neurons that lack PS1 (Naruse, S., et al., 1998 *Neuron* 21:1213–1221). One hypothesis that explains this result is that PS1 modulates trafficking of the C-terminal fragments that result from cleavage of the βAPP and APLP1 proteins (Naruse, supra).

The possible role of presenilins and gamma-secretase also extends to proteolytic processing of proteins other than βAPP and βAPP-like proteins. For example, it has been previously determined that the presence of PS1 is required for proteolytic cleavage of the Notch protein, which is a single transmembrane domain cell surface receptor that mediates many cell fate decisions in vertebrates and invertebrates (Artavanis-Tsakonas, S., et al., 1996 *Science* 268:225–232; Kopan, R. and Turner, D. 1996 *Curr. Opin. Neurobiol.* 6:594–601; Weinmaster, G. 1997 *Mol. Cell. Neurosci.* 9:91–102). Mutations of the two transmembrane aspartate residues within PS1 inhibits cleavage of Notch proteins (Ray, W. J., et al., 1999 *J. Biol. Chem.* 274:36801–36807). The postulated gamma-secretase cleavage sequence within an S2-cleaved Notch-1 protein (Schroeter, E. H., et al, 1998 *Nature* 393:382–386) has no similarity with commonly accepted protease cleavage site motifs.

The role of the presenilins and gamma-secretase can be settled by isolating a protein or a protein complex having the functional-activity of gamma-secretase. In general, it is difficult to isolate functionally-active integral-membrane proteins and protein complexes, as they tend to lose their functional activity during the isolation procedure. This difficulty has been overcome by the development of various methods that are described herein.

In addition, the present invention provides an isolated protein complex having gamma-secretase activity. The isolated gamma-secretase protein complex of the invention catalyzes cleavage of polypeptide substrates having gamma-secretase cleavage sequences. It is postulated that the gamma-secretase protein complex of the present invention is the putative gamma-secretase which is responsible for the processing pathway that generates the Aβ-42 peptide.

As a preliminary matter, the detection of gamma-secretase activity requires assays capable of reliable, accurate and expedient detection of the presence or absence of gamma-secretase cleavage products. Moreover, where inhibitors of gamma-secretase activity are desired, it would be particularly helpful to accurately screen a large volume of test compounds without undue processing.

The present invention therefore provides homogenous methods for detecting gamma-secretase activity and inhibitors thereof. The discovery and application of homogenous assay methods for gamma-secretase activity allows for detection of activity without necessitating the steps of isolating and retrieving gamma-secretase cleavage products. The elimination of these steps, for isolating and retrieving cleavage products, provides obvious benefits in terms of speed and accuracy. In addition, the present invention provides homogenous methods for detecting specific products of gamma-secretase activity, including the detection of Aβ or the 6 kDa fragment.

SUMMARY OF THE INVENTION

The present invention provides the discovery that gamma-secretase is an integral membrane protein that is found in the endoplasmic reticulum, Golgi apparatus, and plasma membrane of various mammalian cell types.

The present invention provides an isolated protein that catalyzes the proteolytic cleavage of a substrate, such as a βAPP polypeptide; the functionally-active protein complex is described herein as a gamma-secretase, e.g., a gamma-secretase complex. The present invention provides an isolated cell-free membrane fraction which includes functionally active gamma-secretase. The present invention also provides a gamma-secretase protein complex that is isolated in a solubilized form.

The present invention provides methods for isolating the gamma-secretase protein by co-isolating it with PS1. Additionally, the present invention provides methods for isolating solubilized integral-membrane proteins or protein complexes, such as the gamma-secretase complex.

In addition, the present invention provides a composition, comprising N-3[(dimethylamino) propyl]3,7, 12-trihydroxy (3a,5b,7a,12a) cholan-2-amide] and CHAPSO™; the novel composition is useful for isolating the gamma-secretase protein complex, reconstitution methods, isolating a substrate, and identifying reagents that inhibit gamma-secretase activity.

The present invention also provides methods for detecting gamma-secretase activity and for detecting the production of gamma-secretase products, particularly, Aβ. In addition, the present invention provides methods for identifying reagents that inhibit gamma-secretase activity.

To identify gamma-secretase inhibitors, a test compound is introduced to a sample containing uncleaved βAPP, βAPP fragments, and gamma-secretase. The gamma-secretase is activated and the effect of the test compound on the amount of gamma-cleaved βAPP fragment produced is monitored. Where β-secretase has cleaved fragments or is also present, the amount of Aβ can be monitored.

In particular, the present invention provides an efficient system for detecting the cleavage of βAPP substrates by gamma-secretase in fluid samples, namely by measuring the production of gamma-cleaved βAPP fragments. The detection system utilizes a pair of fluorescent adducts which are capable of transferring fluorescent energy from one to the other. By using the pair as labels for the substrates and products of gamma-secretase, the activity of gamma-secretase can be monitored.

The binding assay operates by binding each of the fluorescent adducts as labels to different portions of the same gamma-cleaved βAPP fragment. In a preferred embodiment of the invention, the first of the fluorescent adducts binds specifically to the carboxy terminal end of a gamma-cleaved βAPP fragment, at the site of normal gamma-secretase cleavage, i.e., at amino acid residue 711 (corresponding to Aβ amino acid residue 40), while the second fluorescent adduct binds to a portion of the same gamma-cleaved βAPP fragment in the amino terminal region, in amino acids 1 through 702. Most preferably, particularly where Aβ detection is also an objective, the second fluorescent adduct binds within an amino acid sequence corresponding to amino acid sequence 1–31 of Aβ. Optionally, it can be conceived that the first fluorescent adduct may instead specifically bind to the carboxy terminal end of a gamma-cleaved βAPP fragment at amino acid 713 (Aβ amino acid residue 42), the cleavage site most commonly associated with mutations in βAPP, PS1 or PS2. Preferably, the fluorescent adducts do not bind to overlapping sites of the gamma-cleaved βAPP fragment, and the first fluorescent adduct, which is specific to the gamma-cleaved βAPP at its carboxy terminal end, has substantially no cross-reactivity to either uncleaved βAPP or to other types of gamma-cleaved βAPP fragments. Gamma-secretase cleavage is detected when excitation of one of the bound fluorescent adducts provides a detectable transfer of energy to the other fluorescent adduct.

In an alternative embodiment for the detection of gamma-secretase cleavage, the adducts bind to separate cleavage products. Each of the fluorescent adducts would bind to separate amino acid sequences corresponding to opposite sides of the gamma-secretase cleavage site on an uncleaved βAPP. Preferably in this alternative embodiment, at least one of the fluorescent adducts binds to its amino acid sequence with substantially no cross-reactivity to other portions of uncleaved βAPP. Where gamma-secretase cleavage has occurred, the fluorescent adducts would each be bound to their separate gamma-cleaved βAPP fragments, thus resulting in a substantially decreased transfer of energy upon excitation.

BRIEF DESCRIPTION OF FIGURES

FIG. 1: (A) A schematic representation of the recombinant vector that encodes the βAPP (C-100) polypeptide substrate; (B) a schematic representation of the recombinant vector that encodes the βAPP (C-83) polypeptide substrate.

FIG. 2: The nucleotide (SEQ ID NO:1) and amino acid (SEQ ID NO:2) sequence of the recombinant βAPP (C-100) polypeptide substrate.

FIG. 3: The nucleotide (SEQ ID NO:3) and amino acid (SEQ ID NO:4) sequence of the recombinant βAPP (C-83) polypeptide substrate.

FIG. 4: The amino acid sequence of beta-secretase cleaved, human βAPP which is recognized and cleaved by gamma-secretase (SEQ ID NO:10).

FIG. 5: The amino acid sequence of S2-cleaved, human Notch-1 which is recognized and cleaved by gamma-secretase (SEQ ID NO:11).

FIG. 6: Detection of the radio-labeled 6 kDa gamma-secretase cleavage product resulting from a cleavage reaction that includes the solubilized gamma-secretase complex.

FIG. 7: Detection of the cleavage products of the C83 and C100 substrates resulting from a cleavage reaction that includes the solubilized gamma-secretase complex.

FIG. 8: Detection of the cleavage products of the C100 substrate resulting from a cleavage reaction that includes the immunoisolated gamma-secretase complex.

FIG. 12: A list illustrating the chemical structures of the preferred donor molecules.

FIG. 13: A list illustrating the chemical structures of some of the preferred acceptor molecules, including preferred quencher molecules.

DETAILED DESCRIPTION OF THE INVENTION

Terminology

Figure 9:
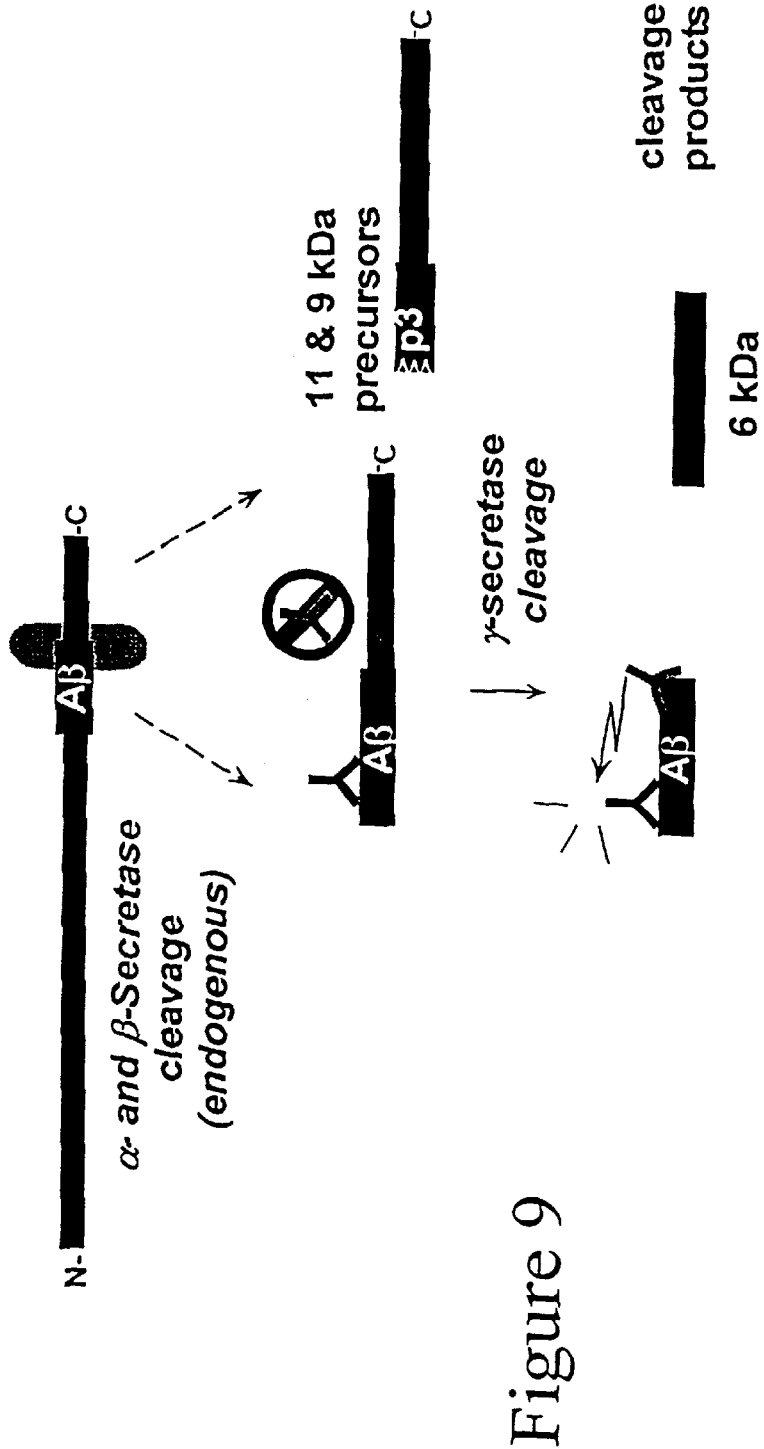
FIG. 9: A schematic representation of a time-resolved fluorescence method for detecting cleavage of a gamma-secretase substrate.

As used herein, the term "isolated" refers to a gamma-secretase protein or protein complex that has been separated away from the phospholipid bilayer, and from other integral-membrane proteins and protein complexes.

As used herein, the terms "gamma-secretase protein" and "gamma-secretase" refer to a protein that exhibits gamma-secretase activity which includes: recognizing a polypeptide substrate having a gamma-secretase cleavage sequence; and catalyzing cleavage of the gamma-secretase cleavage sequence, at the gamma-secretase cleavage site, to produce substrate cleavage products.

As described herein, the terms "gamma-secretase protein complex" and "gamma-secretase complex" refer to a protein complex comprising at least two protein molecules, where at least one of the protein molecules catalyzes cleavage of a polypeptide substrate having a gamma-secretase cleavage sequence. The protein molecules that comprise the gamma-secretase protein complex may associate with each other, in a covalent and/or non-covalent interaction. Additionally, the gamma-secretase protein complex may also include non-proteinaceous molecules, such as vitamins, ATP, or divalent cations.

As used herein, the terms "amino-terminal region" and "carboxy-terminal region" serve as reference points to indicate whether portions of a peptide chain on either side of a particular site (typically the cleavage site for gamma-secretase) fall on the side proximal to the amino-terminus or to the carboxyl terminus, respectively; the portions furthermore may or may not comprise the amino- or carboxy-terminus of the peptide chain. In addition, as described herein, the terms "amino-terminal end" and "carboxy-terminal end" serve as reference points in the same fashion, but are distinguishable from "amino-terminal region" or "carboxy-terminal region" in that they do comprise the amino- or carboxy-terminus, respectively, of the peptide chain.

As used herein, the term "solubilized" refers to an integral membrane protein or protein complex which is separated away from the lipid bilayer (e.g., the membrane bilayer) and other integral-membrane proteins or protein complexes, using a compound that fragments the membrane thereby separating the integral-membrane proteins and protein complexes from the membrane. A typical method to solubilize integral-membrane proteins involves using compounds, such as detergents, which fragment the phospholipid bilayer and provide the integral-membrane proteins or protein complexes with an environment that mimics the chemical characteristics of the phospholipid bilayer, thereby permitting: the solubilized protein or protein complex to fold into the native conformation. Thus, a protein or protein complex that is in a detergent environment is a protein or protein complex that is in solubilized form. Furthermore, the solubilized protein or protein complex may or may not have the biological activity exhibited by the protein or protein complex in its native conformation.

In order that the invention herein described may be more fully understood, the following description is set forth.

The Gamma-secretase Protein of the Invention

Isolated Gamma-secretase Protein

Gamma-secretase protein, when functionally active, cleaves a polypeptide substrate having a gamma-secretase cleavage sequence. Cleavage typically results in substrate cleavage products. The present invention provides gamma-secretase proteins that are isolated, for example, in a detergent-solubilized form. In one embodiment, the gamma-secretase protein comprises a component of the gamma-secretase protein complex. Additionally, the invention provides antibodies (monoclonal, polyclonal, chimeric, humanized, or antibody fragments) reactive with a gamma-secretase protein.

The Functional Activity of Isolated Gamma-secretase

The present invention provides the discovery that the gamma-secretase is an integral membrane protease. Furthermore, the present invention provides isolated membrane fractions and solubilized protein complexes that exhibit the functional activity of gamma-secretase.

The functional activity of gamma-secretase includes: recognizing a polypeptide substrate having the gamma-secretase cleavage sequence; and catalyzing cleavage of the gamma cleavage sequence, at the gamma-secretase cleavage sequence, to generate substrate cleavage products. For example, the isolated gamma-secretase complex cleaves a polypeptide substrate, such as βAPP.

In cells, the gamma-secretase complex cleaves βAPP at the gamma-secretase cleavage site, resulting in the βAPP cleavage products including: the Aβ-40 and -42 peptides, which are substrate cleavage products resulting from beta- and gamma-secretases; the p3 peptide, which is a substrate cleavage product resulting from alpha- and gamma-secretases; the p6 peptide, which is the C-terminal product of cleavage by gamma-secretase; or fragments thereof (reviewed in Haass, C., and Selkoe, D. J. 13 *Cell* 75:1039–1042). The gamma-secretase cleavage sequence of βAPP is known (Duffy, C. L., et al., 1988 *Brain Res.* 474:100–111; Castano, E. M. and Frangione, B. 1988 *Lab. Invest.* 58:122–132).

The Isolated Gamma-secretase Protein Complex

The present invention provides the discovery that the gamma-secretase protein complex can be an integral-membrane protein complex that is typically found in the endoplasmic reticulum and Golgi of various mammalian cell types. Additionally, gamma-secretase protein complexes may be found in the plasma membrane. Furthermore, the gamma-secretase complex can be acidic (pI<5.6), glycosylated, and exhibit a molecular size of approximately 700 kDa.

The gamma-secretase protein complex can be isolated from cells obtained from many species, including mammalian species such as, bovine, ovine, porcine, murine, equine, and preferably, human. Additionally, the gamma-secretase complex may be isolated from species such as plants, insects (such as *D. melanogaster*) and invertebrates (such as *C. elegans*). Furthermore, gamma-secretase may be isolated from any suitable tissue or cells that include the gamma-secretase complex (e.g., gamma-secretase-positive cells). For example, gamma-secretase-positive cells, such as human H4 neuroglioma, and murine N2A neuroblastoma, human embryonic kidney (HEK) 293 cells, COS-1 cells, CHO cells, and HeLa cells. (Haass, C., et al., 1992 *Nature* 359:322–325; Busciglio, J., et al., 1993 *Proc. Natl. Acad. Sci. USA* 90:2092–2096), produce APP cleavage products (e.g., p3, p6, and Aβ peptides).

The gamma-secretase complex may be isolated from cells or tissues that exhibit a wild type phenotype, such as the accumulation of normal levels of APP cleavage products such as Aβ (40 and 42 forms), p3 or p6 peptides. Alternatively, the gamma-secretase complex may be isolated from cells or tissues that exhibit a mutant phenotype, such as the accumulation of higher levels of βAPP cleavage products. The level of accumulated βAPP cleavage products in the mutant tissue/cell is higher when compared to the level of the same cleavage products that are found in a normal tissue/cell source. The tissue/cell that exhibit the mutant phenotype include subjects from any species, or tissues, or cell lines that carry mutated forms of APP, or the PS1 or PS2 protein (reviewed in Tanzi, R., et al., 1996 *Neurobiol. Dis.* 3:159–169).

Components of the Isolated Gamma-secretase Complex

The present invention provides an isolated gamma-secretase complex that includes gamma-secretase with at least one presenilin protein molecule, such as PS1 or PS2, as a protein component. Furthermore, the gamma-secretase complex includes the PS1 or PS2 protein associated with at least one other protein molecule which exhibits gamma-secretase activity. The gamma-secretase complex may or may not be associated with non-proteinaceous components such as vitamins, ATP, divalent cations, or lipids.

The isolated gamma-secretase complex may include more than one PS1 or PS2 molecule that are the same or different polymorphic forms, resulting in a homo-meric or hetero-meric protein complex, respectively. For example, the isolated gamma-secretase complex may include two identical polymorphic forms of PS1 or PS2 molecules, resulting in a homo-meric protein complex. Alternatively, the isolated gamma-secretase complex may include two different forms of PS1 or PS2, resulting in a hetero-meric protein complex. The isolated gamma-secretase complex may include at least one each of PS1 and PS2 molecules.

The present invention provides a gamma-secretase complex that includes at least one variant form of the PS1 and/or PS2 protein molecule, including wild-type, mutant, or splice variant forms. The gamma-secretase complex may be isolated from sources, such as a subject (e.g., from any species), tissue or cell line, that carries a wild-type, mutant, or splice variant form of the PS1 (Sherrington, R., et al., 1995 *Nature* 375:754–760) or PS2 (U.S. Pat. No. 5,986,054).

Methods for Isolating Integral Membrane Proteins
Isolating a Membrane Fraction that Includes the Gamma-secretase Complex The gamma-secretase complex may be isolated as a component of a membrane fraction. For example, conventional methods for isolating a membrane fraction include the following steps: harvesting the cells; lysing the cells to generate the cellular membranes that include peripheral membrane proteins and integral-membrane proteins; collecting the membranes; washing the membranes to remove the peripheral membrane proteins; and isolating the washed membrane fractions. For example, a HeLa cell lysis method is described by Heintz and Roeder (*Proc. Natl. Acad. Sci. USA* 81:2713), and methods for H4 cell lysis and isolating membrane fractions are described by S. B. Roberts, et al., (1994 *J. Biol. Chem.* 269:3111–3116), and methods for the membrane wash are described by P. Walter and G. Blobel (1981 *J. Cell. Biol.* 91:551–556).

Methods for Isolating Integral-membrane Proteins in Solubilized Form

The present invention provides methods for isolating integral-membrane proteins in solubilized form. The methods of the present invention may be used to isolate solubilized proteins and protein complexes that may or may not retain functional-activity. Further, the methods of the present invention may be used to isolate solubilized protein complexes that have the functional-activity of gamma-secretase.

The present invention provides methods comprising the general steps of: solubilizing a membrane with a solution thereby obtaining a mixture having integral membrane proteins, protein complexes and other cell components; and isolating the integral membrane proteins or protein complexes.

The preferred method comprises solubilizing a washed membrane fraction. The integral-membrane proteins and protein complexes which are included in the washed membrane fraction, as described above, may be solubilized (e.g., extracted) from the membrane. The conventional extracting methods (e.g., solubilization step) are typically performed using amphiphilic detergents in aqueous solution. Many different detergents are commercially available, such as ionic and non-ionic detergents, which vary in their dissociating effects, critical micelle concentration (CMC), effect on enzymatic activity, effect on further purification, and ease of removal from the solution. Many different detergents and methods of solubilization of membrane proteins are known to those skilled in the art (Neugebauer 1990 *Methods Enzymol.* 182:239–253; Hjelmiland 1990 *Methods Enzymol.* 182:253–264).

In order to maintain the functional-activity of the integral-membrane proteins and protein complexes that can be lost during the isolation procedure, one embodiment of the invention provides an extraction method using an extraction solution comprising N-[3[(dimethylamino) propyl]3,7,12-trihydroxy (3a,5b,7a,12a) cholan-2-amide], which is an intermediate that occurs in the manufacture of CHAPSO™ (Pierce, Rockford, Ill.). The intermediate N-[3[(dimethylamino) propyl]3,7, 12-trihydroxy (3a,5b,7a,12a) cholan-2-amide] will be referred to herein as "mCHAPSO".

The present invention provides a solution comprising mCHAPSO and the commercially available detergent CHAPSO™. The preferred solution comprises one part (volume/volume) mCHAPSO and two parts CHAPSO™. The preferred solution is useful for isolation of solubilized integral-membrane proteins and protein complexes, such as the gamma-secretase complex.

Methods for Enrichment of the Gamma-secretase Complex

The present invention provides methods for enriching a sample (e.g., a preparation), having solubilized integral-membrane proteins and protein complexes, for the gamma-secretase complex. For example, isolated integral-membrane proteins and protein complexes may be prepared by the solubilization method of the invention, and then enriched for the gamma-secretase complex using conventional techniques, such as immuno-affinity enrichment, cation or anion exchange, lectin-affinity, and/or gel filtration. The enriched gamma-secretase complex will typically exhibit an increase in specific activity, which may be defined as: the amount of substrate cleaved per minute per volume of gamma-secretase protein complex.

Immuno-affinity Enrichment for the Gamma-secretase Complex

The present invention provides methods for isolating gamma-secretase from a sample by isolating gamma-secretase associated with presenilin. The preferred method uses immuno-affinity enrichment methods. For example, the immuno-affinity method includes the following steps: contacting the sample (e.g., the solubilized integral membrane proteins and protein complexes) with an agent that recognizes and binds the presenilin so that an agent/presenilin complex forms; and isolating the agent/presenilin complex from the sample.

The preferred enrichment methods involve using agents, such as anti-presenilin antibodies (e.g., anti-PS1 and/or anti-PS2 antibodies), that bind specifically to the presenilin. However, enrichment by other means is possible and within the skill of those in the art (Table 1). The preferred enrichment methods include contacting the sample with the agent that recognizes and binds the presenilin in a solution comprising mCHAPSO. The preferred solution comprises one part mCHAPSO and two parts CHAPSO™.

In a preferred embodiment, the method includes the following steps: preparing an affinity matrix which specifically binds to the presenilin; equilibrating the affinity matrix with the novel equilibration solution; contacting the equilibrated affinity matrix with the solubilized integral-membrane fraction which includes the gamma-secretase complex (e.g., gamma-secretase associated with a presenilin) under conditions that permit binding of the presenilin to affinity matrix; and removing the proteins that did not bind to the affinity matrix thereby enriching for the gamma-secretase complex. A further step may include eluting the desired protein from the affinity matrix. The general steps and conditions for affinity enrichment for a desired protein or protein complex can be found in *Antibodies: A Laboratory Manual* (Harlow, E. and Lane, D., 1988 CSHL, Cold Spring, N.Y.).

The immuno-affinity matrix may be prepared by: selecting a solid support matrix; and attaching the agent that recognizes and binds to presenilin (e.g., anti-presenilin antibody) to the selected matrix to generate the affinity matrix. The matrix can be selected from a variety of commercially-available solid support matrices, including protein A or G beads, or activated beads. The choice of the matrix used will depend upon the affinity of the matrix for the antibody to be attached. For example, the protein A and G beads exhibit different binding affinity spectrums for various antibodies. The matrix can be attached to the antibody using various coupling methods, including the direct coupling and the high salt direct coupling methods (Gersten, D. M., and Marchalonis, J. J., 1978 *J. Immunol. Methods*, 24:305–309; Schneider, C., et al., 1982 *J. Bio. Chem.* 257:10766–10769). An alternative method involves coupling antibodies to activated beads (Porath, J. and Axen, R. 1976 *Methods Enzymol.* 44:19–45; Scouten, W. H. 1987 *Methods Enzymol.* 135:3065; Harlow, E. and Lane, D., 1988 supra). The preferred matrix for affinity enrichment of the gamma-secretase complex includes the protein A beads. The preferred coupling method includes the direct coupling method using dimethyl suberimidate.

The matrix may be attached to monoclonal or polyclonal antibodies, or a combination thereof, that react specifically with the presenilin. The anti-PS1 and -PS2 antibodies may be raised against a full-length or a fragment of the presenilin protein. The antibodies may be raised against isolated presenilin proteins from naturally-occurring sources, or synthesized by recombinant DNA technology or chemical synthesis methods. The antibodies may have additional amino acid tags, such as cysteine or histidine, to facilitate isolation and purification of the anti-presenilin antibody. Alternatively, the matrix may be attached to antibodies that react specifically with the isolated gamma-secretase complex.

The antibodies may exhibit a range of binding characteristics, ranging from weak to tight binding to the presenilin. For example, the matrix may be attached with anti-PS1 and/or -PS2 polyclonal or monoclonal antibodies for affinity enrichment of the gamma-secretase associated with PS1 or PS2.

In one embodiment, an antibody used for immuno-affinity enrichment of gamma-secretase associated with a presenilin includes a polyclonal antibody (e.g., 1357) which can be raised against a synthetic peptide antigen having the sequence CRDSHLGPHRSTPESR-amide (SEQ ID NO.: 5), matching amino acids 344–358 of human PS1, plus an N-terminal cysteine for coupling the peptide antigen to a carrier protein. Another preferred antibody is a polyclonal antibody (e.g., 1398) which can be raised against a synthetic peptide having the sequence CGHPEPLSNGRPQGNSR-amide (SEQ ID NO.:6), matching amino acids 45–60 of human PS1, plus an N-terminal cysteine for coupling the peptide antigen to a carrier protein. The most preferred affinity matrix for enriching the gamma-secretase complex includes a mixture of the 1357 and 1398 antibodies.

Another preferred antibody is a polyclonal antibody (e.g., SR92) which can be raised against a peptide having the sequence Norleucine-RDSHLGPHRSTPESR-amide (SEQ ID NO.:9).

Another embodiment provides the use of anti-human PS1 antibodies for affinity enrichment of the gamma-secretase complex which antibodies include: JH2 which is a purified polyclonal rabbit antibody raised against a bacterially-expressed PS1 fragment (PS11–77) (SEQ ID NO.:7); and JH5 which is a purified polyclonal antibody raised against the PS1 "loop"—GST fusion protein (SEQ ID NO.:8). The immuno-affinity matrix may be coupled with antibodies that permit elution of the bound gamma-secretase complex under mild elution conditions, such as low pH or glycine. For example, an immuno-affinity matrix coupled with the 1357, 1398, JH2 or JH5 antibodies will permit elution of the bound gamma-secretase complex under relatively mild elution conditions.

The affinity matrix may be equilibrated with the novel equilibration solution. The preferred equilibration solution for affinity enrichment of the desired protein, such as the gamma-secretase complex comprises 1 part (volume/volume) mCHAPSO and 2 parts CHAPSO™.

The solubilized integral-membrane fraction, which includes the desired protein, may be contacted with the affinity matrix under conditions that permit binding of the desired protein with the affinity matrix. The contacting step may be performed in suspension, in solution, or on a column. Typically, the contacting step is performed at 4° C. for a length of time between 1 to 16 hours. The desired protein can adsorb, or bind, to the affinity matrix during the contacting step.

The washing step comprises contacting the affinity matrix that is bound to the desired protein with a wash solution. The preferred wash solution includes the nonionic detergent CHAPSO™ that removes the unbound (e.g., unadsorbed) proteins and protein complexes that are present in the integral-membrane fraction. Typically, the volume of the wash solution used is equivalent to at least 20 times the volume of the affinity matrix.

The eluting step comprises contacting the affinity matrix that is bound to the desired protein with an elution solution that causes the desired protein to become unbound. The elution solution selected will depend on the binding characteristics of the antibody that is coupled to the affinity matrix. Additionally, different elution solutions may be used in combination or in a stepwise manner. For example, the elution solution may include high or low pH, high salt, ionic detergents, dissociating agents (e.g., urea or guanidine HCl), chaotropic agents, organic solvents, and/or water. The preferred elution solution for eluting the gamma-secretase complex from the affinity matrix is a low pH solution (e.g., pH 2.5) that includes glycine and CHAPSO™.

Alternative Enrichment Methods

Alternative methods for enriching a sample for gamma-secretase includes various methods that do not specifically bind to PS1 or PS2. For example, alternative methods include enrichment methods such as: cation exchange chromatography (e.g., Mono S; Pharmacia); anion exchange chromatography (e.g., DEAE Sepharose Fast Flow; Pharmacia); lectin affinity (e.g., Wheat Germ Agglutinin agarose; Amersham Pharmacia Biotech, Piscataway, N.J.); and gel filtration (e.g., Superose 6; Amersham Pharmacia Biotech, Piscataway, N.J.).

In one embodiment, the method provides contacting the sample with a molecule that recognizes and binds a glycosylated-protein (e.g., wheat germ agglutinin) so that a molecule/glycosylated protein complex forms; and removing the molecule/glycosylated protein complex from the sample, thereby enriching the sample for the protein complex having gamma-secretase activity.

The sample of solubilized integral-membrane proteins and protein complexes may be enriched for the gamma-secretase protein or protein complex, using any of a combination of these various enrichment methods. A preferred method for enrichment includes subjecting the solubilized sample to: a cation exchange condition, an anion exchange condition, a lectin affinity condition, and/or a gel filtration condition. The enrichment of the solubilized fraction, as measured by the unit activity of gamma-secretase, increased with the various conditions (Scopes, R. K., 1987 *Protein Purification; Principles and Practice*, Springer-Verlag, NY, N.Y.). For example, the anion exchange condition resulted in approximately a 2-fold enrichment, the lectin-affinity condition resulted in approximately a 46-fold enrichment, and the gel-filtration condition resulted in approximately a 56-fold enrichment (See Table 1).

These results revealed characteristics of the chemical and physical nature of the isolated gamma-secretase complex. For example, the gamma-secretase complex is acidic (pI<5.6; e.g., enrichment with the anion exchange condition), glycosylated (e.g., binds to wheat germ lectin), and is quite large (e.g., >700 kDa; e.g., as determined by gel filtration).

al., 1987 supra), the full-length sequence of the mature βAPP protein (Kang, J., et al., 1987 supra), or a fragment thereof. The preferred substrate includes the transmembrane domain of βAPP. For example, the substrate may be a fragment of the full-length, mature βAPP protein that includes the transmembrane domain, such as the C100 CTF or C83 CTF βAPP cleavage products. The preferred substrate mimics an alpha-cleaved βAPP protein, such as C83 CTF (FIG. 3). Alternatively, the preferred substrate mimics a beta-cleaved βAPP protein, such as C100 CTF (FIG. 2).

In addition, gamma-secretase is postulated to cleave other transmembrane proteins, such as Notch and APLP1. Cleavage occurs within the cytoplasmic half of the domain that spans the membrane (reviewed in: Selkoe, D. J. 1999 *Nature* 399 (6738 Suppl):A23–31; Wang, R., et al., 1996 *J. Biol. Chem.* 271:31894–31902; Schroeter, E. H., et al., 1998 *Nature* 393:382–386), producing heterogeneous cleavage products (Wang, R., et al., 1996 supra). The recognition, and perhaps the availability, of the substrate for cleavage by gamma-secretase may depend upon shortening of the extra-cytosolic domains to within 30 amino acid residues of the extra-cytosolic membrane face (Brown, M. S., et al., *Cell* 100:391–398; Mumm, J. S., et al., 2000 *Molecular Cell* 5:197–206).

A putative gamma-secretase cleavage sequence has been identified in the Notch-I protein (Schroeter, E. H., et al., 1998 *Nature* 393:382–386) (FIG. 5 and SEQ ID NO.:11). Gamma-secretase is also postulated to cleave the APLP1 protein (Wasco, W., et al., 1992 supra). The preferred gamma-secretase substrates include the full-length sequence

TABLE 1

| Fraction | Protein conc'n (mg/ml) | Volume (ml) | Total protein (mg) | Unit Activity (*) | Total Activity (**) | Specific Activity | Fold purif'n |
| --- | --- | --- | --- | --- | --- | --- | --- |
| Detergent extract | 2.1 | 50 | 105 | 12.5 | 625,000 | 6,250 | 1 |
| S-sepharose | — | 50 | — | — | — | — | — |
| DEAE | 1.6 | 22 | 35 | 17.9 | 393,250 | 11,235 | 1.9 |
| Wheat germ | 0.06 | 22 | 1.3 | 16.4 | 360,250 | 277,115 | 46 |
| Superose-6 | 0.013 | 22.5 | 0.3 | 4.75 | 106,875 | 365,250 | 59 |

\* = fmol substrate cleaved/min/μl
\*\* = fmol/min/mg

Substrates For Gamma-secretase

The present invention provides gamma-secretase substrates, which are proteins and polypeptides, that can be cleaved by a protease having gamma-secretase activity. The substrate can be cleaved at the gamma-secretase cleavage sequence to generate the appropriate cleavage products. Additionally, the invention provides antibodies (monoclonal, polyclonal, chimeric, humanized, or antibody fragments) reactive with the substrates and cleavage products of the substrates of the invention.

The Gamma-secretase Cleavage Sequence

The gamma-secretase cleavage sequence is an amino acid sequence that is recognized and cleaved by gamma-secretase. The gamma-secretase cleavage sequence has been previously identified in βAPP (reviewed in Haass, C. and Selkoe, D. J. 1993 *cell* 75:1039–1042) (FIG. 4 and SEQ ID NO.: 10). The gamma-secretase substrates are proteins or polypeptides that include the gamma-secretase cleavage sequence which is recognized and cleaved by a protein or protein complex having gamma-secretase activity. Accordingly, the gamma-secretase substrates include the full-length sequence of the βAPP pre-protein (Kang, J., et of the Notch-i protein (Schroeter, E. H., et al, 1998 supra; Mumm, J. S., et al., 2000 *Molecular Cell* 5:197–206), the APLP1 protein (Wasco, W., et al., 1992 supra), or fragments thereof.

The Structure of the Substrate

The gamma-secretase substrates also include a transmembrane domain which may be folded into a structure that is similar or identical to the native conformation found in substrates such as βAPP, Notch, or APLP1. The native conformation refers to the folded structure of a naturally-occurring protein. For example, the native conformation of an integral-membrane protein is the folded structure of the protein as it is found in the naturally-occurring membrane. In a similar manner, the native conformation of an integral-membrane protein complex is the folded structure of the protein complex as it is found in the naturally-occurring membrane.

The substrate can fold into the native conformation when a membrane-like environment surrounds it. For example, the membrane-like environment may be provided by a membrane fraction, microsomes, or a detergent used to solubilize integral membrane proteins. Accordingly, the substrates may be isolated as a protein component in a membrane fraction or a microsome, or as a detergent-solubilized substrate. The preferred substrate is a polypeptide that is surrounded by a microsomal membrane. The more preferred substrate is a polypeptide that is isolated in detergent-solubilized form.

Methods for Isolating The Gamma-secretase Substrates

The polypeptide substrates that can be cleaved by the gamma-secretase complex may be generated by various methods. For example, the substrates may be isolated as a component of a membrane fraction from naturally-occurring sources, such as tissue samples or cell cultures (Seubert, P. supra; Shoji, M. supra; Haass, C. supra; Busciglio, J. supra). Alternatively, the substrates may be generated using recombinant DNA technology (Sambrook, et al., 1989 in *Molecular Cloning, A Laboratory Manual*, Cold Spring Harbor Press, Plainview N.Y.; and Ausubel, F., et al., 1989 *Current Protocols in Molecular Biology*, John Wiley & Sons, New York, N.Y.), using the nucleotide sequences that encode the βAPP (Haass, C. and Selkoe, D. J. 1993 supra), Notch (Schroeter, E. H., et al., 1998 supra), or APLP1 (Kang, J., et al., 1987 supra; Wasco, W., et al., 1992 supra) proteins or polypeptides and a host-vector system. The substrates may also be generated by chemical synthesis technology (Dugas, H. and Penney, C. 1981 in: *Bioorganic Chemistry*, pp. 54–92, Springer-Verlag, New York) using the amino acid sequence of βAPP, Notch, or APLP1 as a basis for synthesizing the polypeptide. The substrates may also be generated by in vitro transcription-translation methods (Pelham, H. R. B. and Jackson, R. J. 1976 *Eur. J. Biochem.* 67:247; Krieg, P. and Melton, D 1984 *Nucl. Acids. Res.* 12, 7057).

The preferred substrates are generated in a form that is surrounded by a membrane-like environment, such as a microsome membrane or a detergent that mimics a membrane-like environment (e.g., solubilized form). The more preferred substrates are generated in a microsomal membrane form which lacks endogenous gamma-secretase activity. For example, commercially-available canine pancreatic microsomes do not exhibit endogenous gamma-secretase activity (Promega, Madison, Wis.). The most preferred substrates are generated by solubilizing (e.g., extracting) the substrate from microsomal membranes which lack endogenous gamma-secretase activity.

The substrates generated by any of these methods may be labeled with a detectable marker. Examples of a detectable marker include, but are not limited to, a radioisotope, a fluorescent compound, a bioluminescent compound, a chemiluminescent compound, a metal chelator or an enzyme. Technologies for generating labeled polypeptides and proteins are well known in the art (Sambrook, et al., 1989 supra).

Recombinant Molecules Encoding the Substrates

The substrates may be generated using recombinant DNA technology using recombinant molecules (e.g., rDNAs) that encode the substrates or fragments thereof. As used herein, a rDNA molecule is a DNA molecule that has been subjected to molecular manipulation in vitro. Methods for generating rDNA molecules are well known in the art, for example, see Sambrook et al., *Molecular Cloning* (1989), and are useful for producing the substrates.

The present invention provides various nucleic acid molecules having the nucloetide sequences that encode the substrates. The preferred method for generating a substrate uses nucleic acid molecule that encodes a βAPP substrate comprising the signal peptide from the βAPP pre-protein (Kang, J., et al., 1987 supra) linked in-frame to the N-terminal end of the last 100 amino acid residues of the βAPP protein (FIGS. 1A and 2; SEQ ID NO.: 1 and 2). This nucleic acid molecule encodes a βAPP substrate that mimics the C100 C-terminal fragment (CTF).

Another preferred method uses a nucleic acid molecule that encodes a βAPP substrate comprising the APP signal peptide linked in-frame to the N-terminal end of the last 83 amino acid residues of the βAPP protein (FIGS. 1B and 3; SEQ ID NO.:3 and 4). This nucleic acid molecule encodes a APP substrate that mimics the C-83 CTF.

Vectors that Include the Substrate Sequences

Expression vectors may be used to generate the substrates. For example, the nucleotide sequence that encodes the substrate may be operably linked to an expression vector to generate a recombinant expression vector.

The term vector includes, but is not limited to, plasmids, cosmids, and phagmids. A preferred vector includes an autonomously replicating vector, comprising a replicon that directs the replication of the vector within the appropriate host cell. The preferred vectors also include an expression control element, such as a promoter sequence, which enables transcription of the operably linked substrate sequences, and can be used for regulating the expression (e.g., transcription and/or translation) of an operably linked substrate sequence in an appropriate host cell such as *E. coli*. Prokaryote expression control elements are known in the art and include, but are not limited to, inducible promoters, constitutive promoters, secretion signals, enhancers, transcription terminators, and other transcriptional regulatory elements. Other expression control elements that are involved in translation are known in the art, and include the Shine-Delgarno sequence, and initiation and termination codons. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf, D. et al., 1994 *Results Probl Cell Differ* 20:125–62; Bittner et al., 1987 *Methods in Enzymol* 153:516–544).

The preferred vector also includes at least one selectable marker gene that encodes a gene product that confers drug resistance, such as resistance to ampicillin, tetracycline, or kanamycin. Typically, a vector also comprises multiple endonuclease restriction sites that enable convenient insertion of exogenous DNA sequences.

The preferred vectors are expression vectors that are compatible with eukaryotic host cells. The preferred vectors include promoter sequence elements for the production of mRNA transcripts in a reaction with purified bacterial or bacteriophage RNA polymerase. Eukaryotic cell expression vectors are well known in the art and are available from several commercial sources. Typical of such vectors is the pcDNA3 expression vector which is used to express foreign genes in *E. coli*, includes the phage T7 promoter, and confers resistance to ampicillin and G418 (InVitrogen, Carlsbad, Calif.). Other examples include vectors which direct high level expression of fusion proteins that are readily purified. Such vectors include, but are not limited to, the multifunctional *E. coli* cloning and expression vectors such as BLUESCRIPT (Stratagene), in which the substrate coding sequence may be ligated into the vector in frame with sequences for the amino-terminal end Met and the subsequent 7 residues of β-galactosidase so that a hybrid protein is produced; pIN vectors (Van Heeke & Schuster 1989 *J Biol Chem* 264:5503–5509); and the like. The PGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

Host-vector Systems Used to Generate the Substrates

A host-vector system may be used to generate the substrates. The host-vector system includes an appropriate host cell introduced with the recombinant vectors comprising nucleotide sequences encoding the substrate. The host cell can be either prokaryotic or eukaryotic. For example, many commercially-available strains of *Escherichia coli* are particularly useful for expression of foreign proteins. Examples of appropriate eucaryotic host cells include a yeast cell, a plant cell, an insect cell, or an animal cell such as a mammalian cell.

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and maybe chosen to ensure the correct modification and processing of the introduced, foreign protein.

For long-term, high-yield production of recombinant proteins, stable expression is preferred. For example, cell lines which stably express the substrate may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

The recombinant vectors may be introduced into an appropriate cell host by well known methods that typically depend on the type of vector used and host system employed. For example, transformation of prokaryotic host cells by electroporation and salt treatment methods are typically employed, see, for example, Cohen et al., *Proc Acad Sci USA* (1972) 69:2110; and Maniatis et al., (1989) in: Molecular Cloning, A Laboratory Manual, Cold Spring Harbor Laboratory, Cold Spring Harbor, N.Y. Transformation of vertebrate cells with vectors containing rDNAs, electroporation, cationic lipid or salt treatment methods are typically employed (Graham et al., 1973 *Virology* 52:456; Wigler et al., 1979 *Proc. Natl. Acad. Sci. USA* 76:1373–76).

The host cells introduced with the recombinant vectors may be identified by well known techniques. For example, cells resulting from the introduction of the rDNA of the present invention can be cloned to produce single colonies. Cells from those colonies can be harvested, lysed and their DNA content examined for the presence of the rDNA using method such as that described by Southern, *J. Mol. Biol.* (1975) 98:503, or Berent et al., *Biotech.* (1985) 3:208 or the proteins produced from the cell assayed via an immunological method.

Any number of selection systems may be used to recover transformed cell lines. These include, but are not limited to, the herpes simplex virus thymidine kinase (Wigler, M. et al., 1977 *Cell* 11:223–32) and adenine phosphoribosyltransferase (Lowy, I, et al., 1980 *Cell* 22:817–23) genes which can be employed in tk-minus or aprt-minus cells, respectively. Also, antimetabolite, antibiotic or herbicide resistance can be used as the basis for selection; for example, dhfr which confers resistance to methotrexate (Wigler, M. et al., 1980 *Proc Natl Acad Sci* 77:3567–70); npt, which confers resistance to the aminoglycosides neomycin and G-418 (Colbere-Garapin, F. et al., 1981 *J Mol Biol* 150:1–14) and als or pat, which confer resistance to chlorsulfuron and phosphinotricin acetyltransferase, respectively. Additional selectable genes have been described, for example, trpB, which allows cells to utilize indole in place of tryptophan, or hisD, which allows cells to utilize histinol in place of histidine (Hartman, S. C. and R. C. Mulligan 1988 *Proc Natl Acad Sci* 85:8047–51). Recently, the use of visible markers has gained popularity with such markers as anthocyanins, β-glucuronidase and its substrate, GUS, and luciferase and its substrate, luciferin, being widely used not only to identify transformants, but also to quantify the amount of transient or stable protein expression attributable to a specific vector system (Rhodes, C. A., et al., 1995 *Methods Mol Biol* 55:121–131).

In yeast host cells, a number of vectors containing constitutive or inducible promoters such as -factor, alcohol oxidase and PGH may be used (Ausubel, F., et al., 1989 in: *Current Protocols in Molecular Biology*, John Wiley & Sons, New York, N.Y.; Grant, et al., 1987 *Methods in Enzymology* 153:516–544).

In cases where plant expression vectors are used, the expression of a sequence encoding the substrates may be driven by any of a number of promoters. For example, viral promoters such as the 35S and 19S promoters of CaMV (Brisson et al., 1984 *Nature* 310:511–514) may be used alone or in combination with the omega leader sequence from TMV (Takamatsu et al., 1987 *EMBO J.* 6:307–311). Alternatively, plant promoters such as the small subunit of RUBISCO (Coruzzi et al., 1984 *EMBO J.* 3:1671–1680; Broglie et al., 1984 *Science* 224:838–843); or heat shock promoters (Winter, J. and Sinibaldi, R. M. 1991 *Results Probl. Cell. Differ.* 17:85–105) may be used. These vectors can be introduced into plant cells by direct DNA transformation or pathogen-mediated transfection (Hobbs, S., 1992 in: *McGraw Yearbook of Science and Technology*, McGraw Hill New York, N.Y., pp 191–196; Weissbach and Weissbach 1988 in: *Methods for Plant Molecular Biology*, Academic Press, New York, N.Y., pp. 421–463).

An alternative expression system which could be used to express the substrates is an insect system. In one such system, *Autographa californica* nuclear polyhedrosis virus (AcNPV) is used as a vector to express foreign genes in *Spodoptera frugiperda* cells or in Trichoplusia larvae. The substrate-encoding sequence may be cloned into a nonessential region of the virus, such as the polyhedrin gene, and placed under control of the polyhedrin promoter. Successful insertion of the substrate sequence will render the polyhedrin gene inactive and produce recombinant virus lacking coat protein. The recombinant viruses are then used to infect *S. frugiperda* cells or Trichoplusia larvae in which the substrate is expressed (Smith et al., 1983 *J Virol* 46:584; Engelhard, E. K. et al., 1994 *Proc Nat Acad Sci* 91:3224–7).

In mammalian host cells, a number of viral-based expression systems may be utilized. In cases where an adenovirus is used as an expression vector, a substrate coding sequence may be operably linked into an adenovirus vector including adenoviral late promoter (e.g., for transcription) and tripartite leader sequence (e.g., for translation). Insertion in a nonessential E1 or E3 region of the viral genome will result in a virus capable of expressing the substrate in the infected host cells (Logan and Shenk 1984 *Proc. Natl. Acad. Sci.* 81:3655–59). In addition, transcription enhancers, such as the rous sarcoma virus (RSV) enhancer, may be used to increase expression in mammalian host cells.

Host-vector Methods for Generating the Substrates

In general terms, the production of the substrates, involving a host/vector system typically involves the following steps. First, a nucleic acid molecule is obtained that encodes a substrate, such as any one of the polynucleotide sequences disclosed in SEQ ID NOs.: 1 or 3. The substrate-encoding nucleic acid molecule is then preferably inserted into an expression vector in operable linkage with expression control sequences, as described above, to generate a recombinant expression vector that includes the substrate-encoding sequence. The expression vector is then introduced into a suitable host, by standard transformation methods, and the resulting transformed host is cultured under conditions that allow the in vivo production of the substrate. For example, if expression of the substrate sequence is under the control of an inducible promoter, then the growth conditions would include the appropriate inducer. The recombinant vector can integrate the substrate sequence into the host genome. Alternatively, the recombinant vector can maintain substrate sequence extra-chromosomally, as part of an autonomously replicating vector. The substrate, so produced, is isolated from the growth medium or directly from the cells; recovery and purification of the protein may not be necessary in some instances where some impurities may be tolerated.

A skilled artisan can readily adapt an appropriate host/expression system known in the art for use with substrate-encoding sequences to produce the substrates (Cohen et al., 1972 *Proc. Acad. Sci. USA* 69:2110; and Maniatis et al., 1989 *Molecular Cloning, A Laboratory Manual*, Cold Spring Harbor Laboratory, Cold Spring Harbor, N.Y.). Examples of various protein purification methods can be found in *Strategies for Protein Purification and Characterization* (1996) pp 396, Marshak, D. R., et al.

In vitro Transcription-translation Methods to Generate the Substrates

The substrates may be generated in vitro using transcription-translation methods well known in the art. For example, in vitro translation methods include the rabbit reticulocyte (Pelham, H. R. B. and Jackson, R. J. 1976 *Eur. J. Biochem.* 67:247) and wheat germ lysate methods. In general, the reticulocyte methods involve reacting an RNA template that encodes the desired protein, with cellular translation components (e.g., ribosomal proteins, rRNA, and tRNA) and amino acids, under conditions that permit translation of the RNA template into the encoded protein. The RNA template may be mRNA isolated from cells or tissues. The RNA template may also be generated from a DNA template using recombinant DNA technology, such as the pGEM system which uses the SP6/T7 transcription promoters (Promega, Madison, Wis.). Additionally, detectable markers, such as radiolabeled isotopes, may be included in the translation reaction to generate proteins that are radiolabeled. Various in vitro translation systems isolated from rabbit reticulocytes or wheat germ are available commercially (Promega, Madison, Wis.).

Alternatively, the substrate may be generated using a coupled transcription-translation system. In general, the coupled system involves reacting a DNA template that encodes the desired protein, with transcription and translation components, under conditions that permit transcription and translation of the DNA template into the encoded protein. For example, the TNT™ system (Promega, Madison, Wis.) involves using a vector that includes a promoter sequence that is recognized by a highly specific RNA polymerase, such as a T3, T7, or SP6 promoter. The DNA sequence that encodes the desired protein can be operably linked to the promoter to generate a recombinant vector that will serve as the DNA template. The DNA template can be reacted with the transcription and translation components, such as an RNA polymerase, ribonucleotides, translation components and amino acids. Additionally, detectable markers, such as radiolabeled isotopes, may be included in the translation reaction to generate proteins that are radiolabeled. Various coupled systems are commercially available (Promega, Madison, Wis.).

Methods for Generating Microsomal Substrates

The present invention provides methods for generating the microsomal form of the substrate. The methods may include the following steps: (1) inserting a polypeptide substrate comprising a gamma-secretase cleavage sequence into a microsomal membrane, thereby generating a microsomal membrane having a polypeptide substrate that is cleavable by gamma-secretase; and (2) isolating the microsomal membrane having the polypeptide substrate that is cleavable by gamma-secretase.

The substrate may be generated by performing the coupled transcription-translation procedure in the presence of microsomal membranes (Walter, P. and Blobel, G. 1983 *Meth. Enzymology* 65, 856). The coupled transcription-translation procedure may be performed using a nucleic acid molecule (e.g., DNA or RNA) that encodes a polypeptide having the gamma-secretase cleavage sequence. During this procedure, the translated substrate is inserted into and folded within the microsomal membrane, to generate a microsomal membrane having a polypeptide substrate that can be recognized and cleaved by gamma-secretase. The lipid bilayer of the microsomal membranes provides a membrane environment that permits the inserted protein to fold within a membrane environment. The preferred method for generating microsomal substrates includes using microsomal membranes that do not exhibit endogenous gamma-secretase activity, such as canine pancreatic microsomes (Promega, Madison, Wis.).

Methods for Generating the Solubilized Substrate

The present invention provides methods for generating the gamma-secretase substrate in detergent-solubilized form. The preferred method isolates the solubilized substrate from a microsomal membrane which is inserted with a polypeptide having the gamma-secretase cleavage sequence. The general steps of the method include: (1) solubilizing a polypeptide substrate from the microsomal membrane; and (2) isolating the gamma-secretase substrate from the microsomal membrane.

The polypeptide substrate may be extracted from the microsomes using an extraction solution comprising N-[3 (dimethylamino)propyl]3,7,12-trihydroxy (3a,5b,7a,12a) cholan-2-amide] and CHAPSO™. The preferred extraction solution comprises 1 part (volume/volume) N-[3 (dimethylamino) propyl]3,7,12-trihydroxy (3a,5b,7a,12a) cholan-2-amide] and 2 parts CHAPSO™.

Reconstitution Methods for Detecting Gamma-secretase Activity

Reconstitution Methods Using Isolated Membrane Fractions

The invention provides methods for cleaving isolated gamma-secretase substrate. This is also referred to here as a "reconstitution" method which includes detecting gamma-secretase activity by cleaving isolated gamma-secretase substrates. As used herein, the term "reconstituted" method refers to an assay that combines an isolated catalytic protein (e.g., a protease) with a separately isolated substrate, in order to test the functional activity of the catalytic protein. General reconstitution methods are well known in the art (Jackson, R. C. and Blobel, G. 1977 *J Cell Biol* 12:5508; Zwizinski and Wickner 1980 *J Biol Chem* 255: 7973).

For example, a reconstituted system may combine an isolated protease and an isolated substrate in order to test the ability of the protease to cleave the substrate. The isolated protease may be a gamma-secretase protein, a gamma-secretase protein complex, or a membrane fraction which includes gamma-secretase activity. Typically, the reconstituted system is incubated under conditions that are suitable for functional activity of the catalytic protein.

In one embodiment of the invention, the method provides contacting the isolated gamma-secretase substrate of the invention with an isolated gamma-secretase protein or protein complex of the invention, and incubating the substrate so contacted under conditions that permit the gamma-secretase to cleave the substrate. The substrate may be contacted in a solution which includes mCHAPSO. The preferred reaction solution includes one part mCHAPSO and two parts CHAPSO™.

In another embodiment, the present invention provides reconstitution methods for detecting gamma-secretase activity in an isolated membrane fraction. This method includes: incubating the isolated membrane fraction with a separately isolated gamma-secretase substrate (as opposed to endogenous substrate, if any); and incubating the contacted membrane fraction under conditions that permit the protein having gamma-secretase activity in the membrane fraction to cleave the substrate. Detection of the gamma-cleaved substrate can be effected by using a separately isolated substrate, which is labeled with a detectable marker, to permit clear interpretation of the assay. Alternatively, the gamma-cleaved substrate may be detected using immuno-detection methods, such as antibodies reactive against the newly generated termini of the cleaved gamma-secretase substrate.

Detecting the Cleavage Products

The invention also provides methods for detecting gamma-secretase activity in a sample or an isolated protein of interest by detecting the presence of cleavage products. The cleavage products resulting from gamma-secretase activity may be monitored and detected using various methods, including immuno-detection methods. For example, the cleavage products may be immunoprecipitated using antibodies that react specifically with the N— or C-terminus of the Aβ peptides and resolved on a standard SDS/PAGE gel (Citron, M., et al., 1996 *Proc. Natl. Acad. Sci. USA* 93:13170–13175). A variation of this method involves simultaneously detecting the presence of the various Aβ peptides by immunoprecipitation and resolving the 40-and 42-peptide forms on a Bicine/Tris SDS/Urea gel (Klafki, H. -W., et al., 1996 *J. Biol. Chem.* 271:28655–28659) or via mass spectrometry (Wang, R., et al., 1996 *J Biol Chem.* 271:31894–902). Another method involves ELISA assays (Wolfe, M. S., et al., 1999 *Biochemistry* 38:4720–4727; Vassar, R., et al., 1999 *Science* 286:735–741).

Alternatively, the substrate may be labeled with a detectable marker, such as a radiolabel, and the cleavage products may be detected in a gel. For example, the suitable markers may be labeled with $^{35}$S-Met radiolabel and the cleavage products may be resolved and detected in a standard SDS-PAGE gel.

The amount of cleavage product or products may be measured by various methods, including immunologic, chromatographic, or electrophoretic. The amount of cleavage product(s) resulting from reconstitution assays may be used to determine whether the gamma-secretase complex used in a particular assay is functionally-active, mutant, or inhibited by an agent which inhibits the activity of gamma-secretase. For example, the amount of cleavage products resulting from a reconstitution assay using a gamma-secretase complex which is known to be functionally-active may be used as a comparative standard to be compared with the amount of cleavage products resulting from an experimental reconstitution assay using a gamma-secretase complex having an unknown activity, or a gamma-secretase complex which is reacted with an agent having an unknown inhibitory effect on gamma-secretase. An experimental reconstitution assay which exhibits a lack of cleavage products, or a detectable decrease in the amount of cleavage products, compared to the amount in the comparative standard assay indicates that the experimental assay involved a reduced-functional gamma-secretase, a non-functional gamma-secretase, or an agent that inhibits gamma-secretase activity.

Methods for Identifying Inhibitors of Gamma-secretase

The isolated gamma-secretase proteins of the invention (e.g., complexes, in membrane, solubilized, or various enriched forms) are useful for screening strategies that may identify agents that bind and/or cause a change in the activity of gamma-secretase. For example, agents may activate or inhibit the activity of gamma-secretase. The preferred agent will inhibit gamma-secretase activity. These agents may be useful for treating afflictions associated with elevated levels of the Aβ peptides, such as Alzheimer's disease.

The general method for identifying candidate agents that bind to the isolated gamma-secretase complex of the invention comprises the following steps. Isolating the gamma-secretase of the present invention; contacting the gamma-secretase with an agent of interest; and detecting whether the agent inhibits gamma-secretase by any suitable means including those discussed above. The preferred method includes contacting the gamma-secretase in the presence of a solution which includes mCHAPSO.

The screening assay may be performed in a manner similar to the reconstitution methods described herein, using the isolated gamma-secretase complex in the membrane form, the solubilized form, or any of the various enriched forms.

The candidate agents may be, for example, a ligand which is typically a polypeptide, a nucleic acid molecule, an organic molecule, vitamin derivatives, or a metal. A skilled artisan can readily recognize that there is no limit as to the structural nature of the agents used in the present screening methods. The agents can be synthetic or naturally-occurring compounds, such as cellular constituents. The cellular extracts tested in the methods of the present invention can be, as examples, aqueous extracts of cells or tissues, organic extracts of cells or tissues or partially purified cellular fractions.

The polypeptide agents can be generated using standard solid phase or solution phase peptide synthesis methods, as is known in the art. In addition, the nucleic acid molecules encoding these peptides may be generated using standard recombinant DNA technology or synthesized using commercially-available oligopeptide synthesis instrumentation.

The antibody agents can be immunoreactive with selected domains or regions of the gamma-secretase complex. In general, antibodies are obtained by immunization of suitable mammalian subjects with peptides, containing as antigenic regions, those portions of the gamma-secretase complex intended to be targeted by the antibodies.

As used herein, an agent is said to antagonize the activity of the gamma-secretase when the agent reduces the activity of gamma-secretase, such as by reducing the level of cleavage products. The preferred antagonist will reduce the activity of gamma-secretase by more than 50%, more preferably by more than 90%, and most preferably eliminate all activity.

As used herein, an agent is said to agonize the activity of gamma-secretase when the agent increases the activity of gamma-secretase, such as increases the level of cleavage products.

A Rapid Method for Identifying Agents of Interest that Inhibit the Cleavage Activity of Membrane Fraction Having Gamma-secretase Activity An isolated membrane fraction which includes the endogenous gamma-secretase complex and endogenous substrate is useful for relatively rapid methods for screening agents that inhibit the activity of gamma-secretase. Isolated membrane fractions that preserve the integrity of the endogenous substrates are known (Roberts, S et al. 1994 supra). For example, membrane fractions can be made from HeLa cells which express endogenous gamma-secretase and substrates such as the Swedish variant of βAPP ("βAPP$^{sw}$").

The isolated membranes can be used to screen candidate agents that inhibit the activity of gamma-secretase. The cleavage products of the endogenous substrates may be monitored and detected using antibodies that bind specifically with the N- or C-terminal ends of the cleavage products. For example, antibodies that bind the N-terminal region (e.g., 26D6-B2-B3®, SIBIA Neurosciences, La Jolla, Calif.) or bind the C-terminal end (e.g., 9S3.2® antibody, Biosolutions, Newark, Del.) of the Aβ peptide are known. Furthermore, the antibodies may be modified with a pair of fluorescent adducts that transfer fluorescent energy when the adducts are brought in close proximity as a result of binding to the N— or C-terminal ends or regions of the Aβ peptides (FIG. 9). A lack of fluorescence is indicative of the absence of cleavage products, resulting from inhibition of gamma-secretase activity.

As described herein, the term "gamma-cleaved APP fragment" of the present invention refers to any one of several types of βAPP or βAPP fragments which have been cleaved by gamma-secretase at its gamma cleavage secretase site, i.e. 6 kDa C-terminal fragments, p3 fragments, Aβ-40 and -42 peptides and large N-terminal products. For instance, where β-secretase has also cleaved or is present, a gamma-cleaved βAPP fragment may be either a Aβ-40 or -42 peptide or a 6 kDa C-terminal fragment. If α-secretase or β-secretase is not a prerequisite to gamma-secretase activity, then a gamma-cleaved βAPP fragment may be either a 6 kDa C-terminal or a large N-terminal product spanning from the N-terminus of βAPP to the site of gamma-secretase cleavage (approximately 105 kDa when cleaved from the 770 form of βAPP). Moreover, as used herein, the term "uncleaved βAPP" refers to βAPP or βAPP fragments which have not been cleaved by gamma-secretase, but may have been cleaved by α- or β-secretase or by incidental shearing or other means.

As mentioned above, the detection system of the present invention uses a pair of fluorescent adducts to detect the products of gamma-secretase cleavage. As appreciated by one skilled in the art, the fluorescent adducts each comprise a molecule capable of transferring or accepting fluorescent energy, and a functional group which enables linkage of the molecule to a protein or peptide. Well-known functional groups for the purposes of this invention include, but are not limited to, N-hydroxy succinimide ester, maleimido-, iodoacetamido-, or bromoacetamido-functional groups.

One of the fluorescent adducts of the pair comprises a donor molecule which provides fluorescence and is capable of transferring its fluorescent energy to a second molecule. Preferably the donor molecule has long-living fluorescence and may be a lanthanide cryptate or chelate, fluorescein, EDANS, salts of N-[6-amino-9-[2-carboxy-phenyl]-4,5-disulfoxy-3H-xanthen-3-ylidene]aminium ion (2-) such as Alexa Fluor 488® (Molecular Probes, Eugene, Oreg.), salts of 1-(epsilon-carboxypentyl-1'-ethyl-3,3,3',3'-tetramethylindocarbocyanine-5,5'-disulfonate ion such as Cy3® (Amersham Pharmacia Biotech Inc., Piscataway, N.J.) and other donor molecules well known in the art. The chemical structures of the preferred donor molecules are illustrated in FIG. 12. Most preferably, the donor molecule is europium cryptate or chelate.

The other fluorescent adduct in the pair comprises an acceptor molecule which accepts fluorescent energy from the donor molecule. Preferably, the acceptor molecule itself has a short-lived fluorescence at a prescribed wavelength, i.e. xl-APC at approximately 665 nm, but is capable of receiving fluorescent energy from the donor molecule to provide an amplified fluorescent signal. An amplified signal herein refers to a fluorescent signal having a longer duration or greater fluorescent intensity than the signal normally associated with the unpaired acceptor, and may vary with each type of acceptor and/or donor (see Kolb, et al., 1996 in: "Homogeneous Fluorescent technology in High Throughput Screening", *Journal of Biomolecular Screening* 1:203–210). Acceptor molecules that may be used in the present invention include, but are not limited to, derivatives of allophycocyanin, i.e., a cross-linked allophycocyanin ("xl-APC") such as XL665® (Packard Biosciences, Meriden, Conn.), coumarin, rhodamine, tetramethylrhodamine or salts of 1-(epsilon-carboxypentyl)-1'-ethyl-3,3,3',3'-tetramethylindodicarbocyanine-5,5'-disulfonate ion such as Cy5® (Amersham Pharmacia Biotech, Inc., Piscataway, N.J.). The chemical structures of the preferred acceptor molecules are illustrated in FIG. 13. Additional donor and acceptor molecules that would be known to one skilled in the art may be found in Haugland, R. P., *Handbook of Fluorescent Probes and Research chemicals*, Molecular Probes Inc., Eugene, Oreg. (Haugland ed., 6$^{th}$ ed. 1996); Van Der Meer et al. *Resonance Energy Transfer, Theory and Data,* John Wiley and Sons, New York, N.Y. (1991); and Hemmila et al. *Bioanalytical Applications of Labelling Technologies*, Wallac Oy, Turku Finland (Hemmila ed., 2$^{nd}$ ed. 1994).

When bound in close proximity to each other, excitation of the donor molecule provides a detectable transfer of energy to the acceptor molecule. For example, an excited europium cryptate provides a direct transfer of energy to xl-APC, thus providing an amplified signal at about 665 nm (which appears at approximately 660–670 nm). Since europium cryptate has very little fluorescent emission at 665 nm, detection and measurement of a 665 nm fluorescent signal is an indication of the radiation-less fluorescence resonance energy transfer to the acceptor molecule xl-APC when the two fluorescent molecules are in close proximity. Furthermore, since europium cryptate has fluorescence emission at about 620 nm (which appears at approximately 615–625 nm), the measurement of the 620 nm fluorescence provides an internal standard. The ratio of measured 665 nm fluorescence to 620 nm fluorescence can be used as an indication of the proximity of the two fluorescent molecules. Therefore, a detectable transfer of energy is manifested by an amplified signal at the acceptor wavelength (here, about 665 nm), by a change in ratio of the signal between acceptor to donor wavelengths (here 665 nm to 620 nm) as compared to their ratio when unpaired, or by some other normalization of this signal as known to one skilled in the art. Moreover, this normalization technique is not limited to europium cryptate and xl-APC, but may be used with other fluorescent pairs to detect proximal binding, i.e. fluorescein and coumarin, Cy3® and Cy5® (Amersham Pharmacia, Piscataway, N.J.) or fluorescein and tetramethylrhodamine and other pairs well-known in the art.

Detection is performed by excitation of the donor molecule by laser, xenon flash lamp, deuterium-tungsten lamp or other energy sources well known in the art. In the preferred embodiment, the preferred source of excitation is by laser. In particular, when both adducts are bound to the same fragment in close proximity, excitation of the donor fluorescent molecule causes a transfer of fluorescent energy to the acceptor molecule, thus giving off a fluorescent signal at the acceptor's emission wavelength (as described above, at approximately 665 nm for xl-APC). Conversely, when the adducts are not in close proximity (i.e. are unbound or bound on separate fragments), excitation provides a substantially decreased transfer of energy, as signified by little or no amplified signal from the acceptor molecule, by an unchanged ratio of the signal between acceptor to donor wavelengths as compared their ratio when unpaired, or by some other normalization technique well-known in the art.

Alternatively, the acceptor molecule may be a fluorescent quencher molecule that is capable of absorbing fluorescent energy from an excited donor molecule and thereby reducing the donor's fluorescent signal. The fluorescent quencher molecule will not itself give a fluorescent signal and will dissipate the donor molecule's fluorescent energy through heat or molecular motion. Fluorescent acceptor molecules that may be used as quenchers in the present invention include, but are not limited to, dabcyl, salts of 9-[2-[[4-carboxy-piperidin-1-yl]sulfonyl]phenyl]-6-(N-methyl-N-phenyl-amino)-3H-xanthen-3-ylidene]-N-methylbenzenaminium ion such as QSY-7® (Molecular Probes, Eugene, Oreg.) and BHQ-3® (Biosearch Technologies, Inc., Novato, Calif.). The chemical structures of some of the preferred quencher molecules are illustrated in FIG. 13. Additional quencher molecules known to one skilled in the art may be found in Haugland, R. P., Handbook of Fluorescent Probes and Research chemicals, Molecular Probes Inc., Eugene, Oreg. (Haugland ed., 6$^{th}$ ed. 1996); Van Der Meer et al. Resonance Energy Transfer, Theory and Data, John Wiley and Sons, New York, N.Y. (1991); and Hemmila et al. Bioanalytical Applications of Labelling Technologies, Wallac Oy, Turku Finland (Hemmila ed., 2$^{nd}$ ed. 1994).

In contrast to the previously-mentioned acceptor molecules such as xl-APC, a fluorescent quencher molecule will absorb energy from an excited donor when in close proximity on the same fragment and provide no fluorescent signal of its own. Therefore, when in close proximity, a detectable transfer of energy where the acceptor is a quencher molecule is manifested by a decrease in fluorescent signal by the donor as compared to its unpaired signal. Consequently, when not in close proximity and where the acceptor molecule is a quencher, detection of a substantially decreased transfer of energy provides an unchanged fluorescent signal by the donor as compared to its unpaired signal. In both instances, the acceptor provides no signal of its own. Preferred pairings for donor and quencher molecules include, but are not limited to, EDANS and dabcyl, Alexa Fluor 488 and QSY-7® (both available from Molecule Probes, Eugene, Oreg.), and Cy5® (Amersham Pharmacia, Piscataway, N.J.) and BHQ-3® (Biosearch Technologies, Novato, Calif.). Additional pairings of donors and acceptors (or quenchers) may be found by routine experimentation according to one skilled in the art of fluorescent adducts.

The binding, or 'labeling', of gamma-secretase cleavage products by the fluorescent adducts can be direct, semidirect or indirect. For instance, the pair of fluorescent adducts can be directly attached to the uncleaved βAPP, βAPP fragments or gamma-cleaved βAPP fragments, or if semi-direct, one of the fluorescent adducts can be attached to a secondary molecule such as an antibody, or through streptavidin-biotin binding or any other binding technique well-known in the art. Preferably, the binding is indirect, wherein each fluorescent adduct separately modifies an antibody and at least one antibody is specific to an epitope on the gamma-cleaved βAPP fragment with substantially no cross-reactivity to uncleaved βAPP or other types of gamma-cleaved βAPP fragments. Most preferably, the antibodies are monoclonal antibodies and the non-cross-reactive epitope is the cleavage site for gamma-secretase, at either amino acid residue 711 or 713 of the gamma-cleaved βAPP (where the gamma-cleaved βAPP fragment is Aβ, then at amino acid residue 40 or 42).

As described in further detail below, it is possible for one skilled in the art to generate monoclonal antibodies with binding specificity to any desired site on the gamma-cleaved peptides. The ability to generate monoclonal antibodies in turn provides flexibility as to which sites the fluorescent adducts may bind to.

In the preferred embodiment of the invention, the first fluorescent adduct is specific to the gamma-cleaved βAPP fragment at the gamma-secretase cleavage site, ie. the carboxy terminal end comprising amino acid residue 711 of the gamma-cleaved βAPP (if Aβ-40, then amino acid residue 40), and most preferably has no cross-reactivity with uncleaved βAPP or other types of gamma-cleaved βAPP fragments. Where the gamma-secretase cleaves at amino acid residue 713 (if Aβ-42, then amino acid residue 42), the first fluorescent adduct may instead bind to the carboxy-terminal end comprising amino acid residue 713 with substantially no cross-reactivity with uncleaved βAPP or other types of gamma-cleaved βAPP. The second fluorescent adduct may bind to a portion of the same gamma-cleaved βAPP fragment in the amino terminal region, in amino acids 1 through 702. Most preferably, the second fluorescent adduct binds to the gamma-cleaved βAPP within an amino acid sequence which corresponds to amino acid sequence 1–31 of Aβ (see FIG. 4). The corresponding location of Aβ amino acid sequence 1–31 will vary depending on the nature of the gamma-cleaved βAPP fragment: (1) in the p3 fragment, only amino acids 1–15 have correspondence to Aβ, (2) in the large N-terminal fragment, the corresponding amino acid sequence may be in one of three locations, depending on the size of the uncleaved βAPP form (in the 695 form, the corresponding amino acids would be 596–627; in the 750 form, the corresponding sequence would be amino acids 651–682; and in the 770 form, amino acids 671–702), and of course, (3) in the Aβ peptide, the corresponding amino acids would be 1–31. Preferably, the binding site of the first fluorescent adduct does not cross-react to or overlap with the binding site of the second fluorescent adduct. Most preferably, the first fluorescent adduct comprises a donor molecule and further modifies an antibody, while the second fluorescent adduct comprises an acceptor molecule and separately modifies a second antibody.

In the preferred embodiment, the detection system operates by first conducting a cleavage reaction on the βAPP substrates. Cleavage by gamma-secretase is initiated by shifting the temperature from 0 to 37° C., as described in Example 9 below. After cleavage of the substrate, the two fluorescent adducts, which preferably modify monoclonal antibodies, are added to the reaction. Binding of the first and second fluorescent adducts to the same gamma-cleaved βAPP fragments enables a fluorescent energy transfer. The first fluorescent adduct preferably binds to the carboxy terminal end of the gamma-cleaved βAPP fragment, with no substantial cross-reactivity to precursors such as uncleaved βAPP or to other types of gamma-cleaved βAPP fragments. The second adduct will bind to the gamma-cleaved βAPP fragment within an amino acid sequence corresponding to amino acid sequence 1–31 of Aβ, as well as any βAPP precursors or other types of gamma-cleaved βAPP fragments containing the same sequence. Binding of both fluorescent adducts is required to generate a detectable transfer of energy, and to thereby confirm cleavage. Wherein the acceptor is xl-APC or the like, a detectable transfer of energy will be signified by an amplified fluorescent signal at 665 nm. On the other hand, where the acceptor is a fluorescent quencher molecule such as dabcyl, a detectable transfer of energy will manifest as a decreased fluorescent signal by the donor molecule compared to its unpaired state.

The purpose of the detection system is to distinguish the presence of the particular gamma-cleaved APP fragment from uncleaved βAPP or from other types of gamma-cleaved βAPP fragments. The method of detection is homogeneous, which eliminates the steps of separating and retrieving the cleavage products from precursors.

FIG. 9 schematically demonstrates the principle of the detection system in the preferred embodiment where the pair of fluorescent adducts comprises europium cryptate and xl-APC. The βAPP fusion protein is made by cells and is typically cleaved by β-secretase during normal processing. Upon cleavage of βAPP by gamma-secretase, the detection system utilizes the newly-generated binding site to provide a site for the first fluorescent adduct. Meanwhile, the second fluorescent adduct attaches, or may have already attached, in the amino-terminal region of the gamma-cleaved βAPP fragment (here Aβ), as well as to any other βAPP fragments carrying its binding site, irrespective of cleavage by α-, β- or gamma-secretase. The binding of both fluorescent adducts to the same cleaved fragment hence provides a detectable transfer of energy.

In the most preferred embodiment of the invention, one fluorescent adduct comprises europium cryptate and modifies and antibody specific to the carboxy terminal end of the gamma-cleaved βAPP fragment, i.e. at amino acid residue 711 (corresponding to amino acid 40 in Aβ). One antibody which has binding specificity to an epitope comprising amino acid residue 711 (Aβ amino acid 40) is the 9S3.2 antibody (prepared for Bristol-Myers Squibb Co., Princeton, N.J. by Biosolutions, Newark, Del.). Correspondingly, the other fluorescent adduct of the most preferred embodiment comprises x1-APC and modifies a second antibody that binds within the amino-terminal region corresponding to amino acid sequence 1–31 of Aβ (see FIG. 4). An antibody which binds to an epitope corresponding to Aβ amino acid sequence 1–12 is 26D6-B2-B3, which is provided by SIBIA Neurosciences (La Jolla, CA).

In addition to detecting gamma-secretase cleavage, the above detection system can be applied to detect Aβ wherein β-secretase has also cleaved or is present. As mentioned above, detection of Aβ can be accomplished by using a pair of fluorescent adducts which each separately binds to either the amino-terminal region or carboxy-terminal end of Aβ. For example, the above-mentioned embodiment, wherein the pair of fluorescent adducts modify antibodies 9S3.2 and 26D6-B2-B3, would detect any Aβ-40 that may be present. Most preferably, each of the fluorescent adducts separately binds to either the amino- and carboxyl terminal ends of Aβ with substantially no cross-reactivity to each other or to uncleaved βAPP or to other types of gamma-cleaved βAPP fragments. Detection of Aβ would thereby be confirmed when excitation of one fluorescent adduct provides a detectable transfer of energy to the other.

Furthermore, the most preferred embodiment may be modified to detect gamma-secretase cleavage by specific binding to the amino-terminal end resulting from gamma-secretase cleavage, rather than to the carboxy-terminal end. For example, rather than binding to the carboxy-terminal end of the gamma-cleaved βAPP fragment (which typically corresponds to the carboxy-terminal end of the Aβ peptide), the first fluorescent adduct may instead bind specifically to the amino-terminal end of the 6 kDa fragment, with substantially no cross reactivity to uncleaved βAPP or to other types of gamma-cleaved βAPP fragments (i.e., in this modified embodiment, Aβ). In this modified version of the preferred embodiment, the second fluorescent adduct would then bind to the carboxy-terminal region of the 6 kDa fragment. The detection of a transfer of energy in this modified embodiment would thereby signify the presence of the 6 kDa fragment, which is the ubiquitous product of gamma-secretase cleavage irrespective of whether α- or β-secretase is also present.

The detection system can be further modified to screen for inhibitors of gamma-secretase. Test compounds are placed in the assay wells prior to initiating the cleavage reaction, to determine whether the test compounds can competitively inhibit gamma-secretase. The pairs of fluorescent adducts are then added to determine the presence of gamma-cleaved βAPP fragments. In the preferred embodiment described above, wherein the adducts have binding specificity to the carboxyl-terminal end and amino-terminal region, detection of a substantially decreased transfer of energy would then indicate that βAPP has not been cleaved due to inhibition of gamma-secretase.

Still another alternative embodiment for the detection of gamma-secretase cleavage exists, wherein the adducts bind to separate cleavage products. In this alternative embodiment, the fluorescent adducts would bind each to separate amino acid sequences corresponding to opposite sides of the gamma-secretase cleavage site on an uncleaved βAPP. For example, one fluorescent adduct would bind to an amino acid sequence corresponding to the carboxy-terminal region of an uncleaved βAPP, at amino acid sequence 720–770, i.e. the 6 kDa fragment. The other fluorescent adduct binds to the other side of the gamma-secretase cleavage site corresponding to the amino-terminal region of uncleaved βAPP, at amino acid sequence 671–702, i.e. the Aβ peptide or p3 fragment. Preferably in this alternative embodiment, at least one of the fluorescent adducts binds to its amino acid sequence with substantially no cross-reactivity to other portions of uncleaved βAPP. Where gamma-secretase cleavage has occurred, the fluorescent adducts would each be bound to their separate gamma-cleaved βAPP fragments (i.e. the 6 kDa fragment and the Aβ peptide), thus resulting in a substantially decreased transfer of energy upon excitation of the donor molecule.

Furthermore, this alternative embodiment of binding to separate products can be adapted to test for inhibitors of gamma-secretase by the addition of test compounds. Where test compounds are added simultaneously with gamma-secretase, the detection of a transfer of fluorescent energy would then indicate a lack of cleavage by gamma-secretase, and hence, the presence of an inhibitor of gamma-secretase.

The detection system may be performed on samples containing solubilized gamma-secretase, as mentioned previously, or on natural product samples at an appropriate dilution. In the present invention, samples of βAPP substrates can be found in membrane fractions derived from tissue samples or cell cultures. In these samples, the uncleaved βAPP, βAPP fragments and gamma-secretase complex are endogenously produced. As discussed above however, βAPP substrates can be derived from a variety of sources including, but not limited to, recombinant host-vector systems, in vitro transcription-translation, or through organic synthesis of βAPP amino acid sequences, as well as any other reproductive technique well-known in the art.

Methods for Generating Antibodies Directed Against Presenilin and Gamma-secretase Protein Methods for generating antibodies, such as polyclonal, monoclonal, chimeric, and humanized antibodies are well known (Harlow, 1989, *Antibodies: A Laboratory Manual*, Cold Spring Harbor Press, N.Y.) For example, the invention provides antibodies that recognize and bind presenilins, such as PS1 and PS2. Additionally, the invention provides antibodies that recognize and bind gamma-secretase protein or protein complex.

Preferably, the anti-presenilin antibodies will selectively bind to PS1 or PS2 and will not bind (or will bind weakly) to non-presenilin proteins. The preferred anti-gamma-secretase antibodies will selectively bind to gamma-secretase and will not bind to non-gamma-secretase proteins. Anti-PS1, -PS2 or anti-gamma-secretase antibodies include monoclonal and polyclonal antibodies as well as fragments thereof (e.g., recombinant proteins) containing the antigen binding domain and/or one or more complement determining regions of these antibodies. These antibodies can be from any source, e.g., rabbit, rat, dog, cat, pig, horse, mouse and human.

The antibodies may be antibody fragments that specifically recognize a PS1, PS2, or a gamma-secretase protein. As used herein, an antibody fragment is defined as at least a portion of the variable region of the immunoglobulin molecule that binds to its target, i.e., the antigen binding region. Some of the constant region of the immunoglobulin may be included.

Various methods for the preparation of antibodies are well known in the art. For example, antibodies may be prepared by immunizing a suitable mammalian host using a PS1, PS2, or the isolated gamma-secretase protein of the invention, or peptides, or fragments, in isolated or immunoconjugated form (Harlow, 1989, *Antibodies: A Laboratory Manual*, Cold Spring Harbor Press, N.Y.). In addition, fusion proteins of PS1 or PS2 may also be used, such as a PS1 GST-fusion protein. Cells expressing or overexpressing PS1 or PS2 may also be used for immunizations. Similarly, any cell engineered to express PS1 or PS2 may be used. This strategy may result in the production of monoclonal antibodies with enhanced capacities for recognizing endogenous PS1 or PS2.

The amino acid sequence of PS1 (Sherrington, R., et al., 1995 *Nature* 375:754–760) or PS2 (Levy-Lahad, E., et al., 1995 *Science* 269:973–977) may be used to select specific regions of the PS1 or PS2 protein for generating antibodies. For example, hydrophobicity and hydrophilicity analyses of the PS1 or PS2 amino acid sequence may be used to identify hydrophilic regions in the PS1 or PS2 structure. Regions of the PS1 or PS2 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Fragments containing these residues are particularly suited in generating specific classes of anti-PS1 antibodies. Particularly useful fragments include, but are not limited to, the sequences CRDSHLGPHRSTPESR-amide (SEQ ID NO.:5), CGHPEPLSNGRPQGNSR-amide (SEQ ID NO.:6), and Norleucine-RDSHLGPHRSTPESR-amide (SEQ ID NO.:9).

Methods for preparing a protein for use as an immunogen and for preparing immunogenic conjugates of a protein with a carrier such as BSA, KLH, OVA, or other carrier proteins are well known in the art. In some circumstances, direct conjugation using, for example, carbodiimide reagents may be used; in other instances linking reagents such as those supplied by Pierce Chemical Co., Rockford, Ill., may be effective. Administration of a PS1, PS2, or gamma-secretase immunogen is conducted generally by injection over a suitable time period and with use of a suitable adjuvant, as is generally understood in the art. During the immunization schedule, titers of antibodies can be taken to determine adequacy of antibody formation.

While the polyclonal antisera produced in this way may be satisfactory for some applications, for protein isolation, monoclonal antibody preparations are preferred. Immortalized cell lines which secrete a desired monoclonal antibody may be prepared using the standard method of Kohler and Milstein (Nature 256: 495–497) or modifications which effect immortalization of lymphocytes or spleen cells, as is generally known. The immortalized cell lines secreting the desired antibodies are screened by immunoassay in which the antigen is the PS1 or PS2 protein or fragment, or the gamma-secretase protein of the invention. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonal antibodies of the invention or the polyclonal antisera (e.g., Fab, F(ab')$_2$, Fv fragments, fusion proteins) which contain the immunologically significant portion (i.e., a portion that recognizes and binds PS1, PS2, or the gamma-secretase protein) can be used as antagonists, as well as the intact antibodies.

Use of immunologically reactive fragments, such as the Fab, Fab', or F(ab')$_2$ fragments is often preferable. Further, bi-specific antibodies specific for two or more epitopes may be generated using methods generally known in the art. Homodimeric antibodies may also be generated by cross-linking techniques known in the art (e.g., Wolff et al., *Cancer Res.* 53: 2560–2565).

The antibodies or fragments may also be produced, using current technology, by recombinant means. Regions that bind specifically to the desired regions of the PS1 or PS2 protein can also be produced in the context of chimeric or CDR grafted antibodies of multiple species origin.

Alternatively, methods for producing fully human monoclonal antibodies, include phage display and transgenic methods, are known and may be used for the generation of human Mabs (for review, see Vaughan et al., 1998, Nature Biotechnology 16: 535–539). For example, fully human anti-PS1 or -PS2 monoclonal antibodies may be generated using cloning technologies employing large human Ig gene combinatorial libraries (i.e., phage display)(Griffiths and Hoogenboom, Building an in vitro immune system: human antibodies from phage display libraries. In: Protein Engineering of Antibody Molecules for Prophylactic and Therapeutic Applications in Man. Clark, M. (Ed.), Nottingham Academic, pp 45–64 (1993); Burton and Barbas, Human Antibodies from combinatorial libraries. Id., pp 65–82). Fully human anti-PS1 or -PS2 monoclonal antibodies may also be produced using transgenic mice engineered to contain human immunoglobulin gene loci as described in PCT Patent Application WO98/24893, Jakobovits et al., published Dec. 3, 1997 (see also, Jakobovits, 1998, *Exp. Opin. Invest. Drugs* 7(4): 607–614). This method avoids the in vitro manipulation required with phage display technology and efficiently produces high affinity authentic human antibodies.

Reactivity of anti-PS1, or -PS2 mAbs against the target antigen may be established by a number of well known means, including Western blot, immunoprecipitation, ELISA, and FACS analyses using, as appropriate, PS1 or PS2 proteins, peptides, PS1-expressing cells or extracts thereof. Anti-PS1 or -PS2 mAbs may also be characterized in various in vitro assays, including complement-mediated tumor cell lysis, antibody-dependent cell cytotoxicity (ADCC), antibody-dependent macrophage-mediated cytotoxicity (ADMMC), tumor cell proliferation, etc.

The antibody or fragment thereof of the invention may be labeled with a detectable marker, such as a radioisotope, a fluorescent compound, a bioluminescent compound, chemiluminescent compound, a metal chelator or an enzyme.

The following examples are presented to illustrate the present invention and to assist one of ordinary skill in making and using the same. The examples are not intended in any way to otherwise limit the scope of the invention.

EXAMPLE I

The following provides a description of the methods used to generate a gamma-secretase substrate having βAPP sequences, such as the radiolabeled βAPP-C100 or the βAPP-C83 polypeptide mimics. The detergent solution described in Examples 1, 4, 5, 6 and 8, and herein designated "mCHAPSO detergent solution", comprises: 1 part N-[3 [(dimethylamino)propyl]3,7,12-trihydroxy(3a,5b,7a,12a) cholan-2-amide], and 2 parts CHAPSO (Pierce, Rockford, Ill.).

Recombinant Vectors that Encode the BAPP Substrates

The recombinant vector that encodes the human βAPP-C100 polypeptide that mimics the C100 C-terminal fragment (FIGS. 1A and 2) comprises: the pcDNA3 vector (InVitrogen, Carlsbad, Calif.), which carries a phage T7 promoter, DNA encoding APP signal sequence plus amino-terminal end leucine of mature APP (nucleotides 1–54 of APP; Genbank ID Y00264; Kang, J., et al., 1987 *Nature* 325:733–736) linked directly to nucleotide 1936 through 2235 of human βAPP (Genbank Y00264). The recombinant nucleotide sequence encodes the C-100 polypeptide mimic that is detectable as an 11 kDa polypeptide; the nucleotide sequence is described in FIG. 2 and SEQ ID NO.: 1, and the encoded amino acid sequence is described by SEQ ID NO.: 2.

The recombinant vector that encodes the human APP-C83 polypeptide mimic (FIGS. 1B and 3) comprises: the pcDNA3 vector, phage T7 promoter, DNA encoding βAPP signal sequence linked to the sequence CTGGATGCAGAATTC, which is then linked directly to nucleotides 1987–2267 of human APP (Genbank Y00264). The recombinant nucleotide sequence encodes the C-83 polypeptide mimic that is 9 kDa; the nucleotide sequence is described in FIG. 3 and SEQ ID NO.: 3 and the encoded amino acid sequence is described by SEQ ID NO.: 4.

In vitro Transcription and Co-translational Insert of the Polypeptide Mimics into Microsomes The radiolabeled βAPP-C100 and βAPP-C83 polypeptide mimics, inserted into microsomes (e.g., the microsomal substrates), were generated by performing a coupled transcription-translation procedure using the TnT™ Coupled Reticulocyte Lysate System (catalogue # L4610; Promega, Madison, Wis.) and $^{35}$S-methionine (NEN, Boston Mass.) according to the manufacturer's instructions. The co-translational insertion of the radiolabeled βAPP-C100 and -C83 polypeptides into the microsomal membranes was performed by supplementing the Lysate System with canine pancreatic microsomal membranes (catalogue #: Y4041; Promega, Madison, Wis.) at 58 units membranes/400 μl reaction, according to the manufacturer's instructions. Briefly, 600 μl rabbit reticulocyte lysate, 48 μl reaction mixture, 24 μl T7 RNA polymerase, and 24 μl amino acid mixture minus methionine, all from Promega TnT™ Coupled Reticulocyte Translation Kit, were gently mixed together with 24 μl RNAsin™ (Promega, Madison, Wis.), and 100 μl $^{35}$S-methionine. A total of 48 Ig of either βAPPC100 or APP-C83 vector DNA was added and the volume was brought to 1100 μl with double distilled water then mixed by gentle pipetting. Microsomes (172 units, typically ~90 μl) were added and the reaction once again gently mixed, then placed at 30° C. for 75 minutes. The reaction was terminated by placing the tubes on ice.

Isolation of the Microsomal Substrate

The microsomal substrates were isolated by layering 0.4 ml of the transcription-translation reaction on 1.4 ml cushions of ice-cold high-salt sucrose (0.5 M NaCl, 0.5 M sucrose, 20 mM HEPES pH 7.5, 0.5 μM o-phenanthroline, 12 & μg/ml leupeptin). The microsomal substrates were recovered by centrifugation at 4° C., 10 minutes, 100,000 rpm (Beckman TLA 100.3 rotor). The microsomal membrane pellet was gently rinsed, without resuspending, with 1501 of cold low-salt buffer (50 mM HEPES pH 7.5, 0.5 μM o-phenanthroline, 12 μg/ml leupeptin) and the rinse buffer was discarded. The pellet contained the isolated microsomes inserted with the radiolabeled βAPPC100 or βAPP-C83 polypeptides (e.g., the microsomal substrates).

Solubilization of the Polypeptides from the Microsomal Substrate

The radiolabeled βAPPC100 and -C83 polypeptide mimics were extracted from the microsomes in detergent-soluble form using a detergent solution that included "mCHAPSO detergent solution", which comprises: 1 part N-[3 [(dimethylamino)propyl]3,7,12-trihydroxy(3a,5b,7a,12a) cholan-2-amide], and 2 parts CHAPSO (Pierce, Rockford, Ill.).

The microsomal substrate, collected as a pellet, was resuspended in 105 μl of microsomal extraction buffer (50 mM HEPES pH 7.5, 0.5% mCHAPSO detergent solution, 10% glycerol, 1 mM ethylenediaminetetraacetic acid, 1 mM dithiothreitol, 4 μg/ml leupeptin), resulting in the solubilized $^{35}$S-labeled APPC100 or -C83 polypeptide. These solubilized polypeptides were used as substrates. Aliquots of the solubilized radiolabeled APP polypeptides (25 μl) were flash-frozen in liquid nitrogen and stored at –80° C. until use.

EXAMPLE 2

The following provides a description of the methods used to isolate a membrane fraction, which includes integral-membrane proteins embedded within the membrane bilayer.

Harvesting the Cells

Spinner-grown HeLa cells were harvested by centrifuging 1 liter bottles at 1800 rpm×15 minutes x 4° C. The yield was approximately 1 ml of cell pellet per liter. The cells were suspended in ice-cold PBS (catalogue #:14190; Life Technologies, Gaithersburg Md.), using 50× pellet volume. The suspended cells were transferred to 250 ml conical bottle and centrifuged at 1000× G for 10 minutes at 4° C. (Jouan GR 4–22 low speed centrifuge). The cell pellet was resuspended in PBS and the centrifugation step was repeated.

Lysing the Cells

The pellet volume was estimated, 2× the pellet volume of HB Hypotonic Lysis Buffer (10 mM HEPES pH 7.5, 10 mM KCl, 1.5 mM $MgCl_2$) was added, and the cells were carefully resuspended to wash. Immediately before use, 0.5 mM DTT, 0.5 mM PMSF or Pefabloc (Boehringer Mannheim, Indianapolis, Ind.) was added. The cells were centrifuged at 1000× G for 10 minutes at 4° C. (Jouan GR 4–22 low speed). The supernatant was carefully removed, and the cell pellet was incubated on ice for 10 minutes to swell the cells. The cells were broken using a Dounce homogenizer. Briefly, a 20 ml suspension of cells was added to a large dounce homogenizer and homogenized with 15 up-and-down strokes of the "B" pestle. Then 20 ml of additional HB Hypotonic Lysis Buffer was added and mixed with 5 up-and-down strokes of the pestle. The homogenate was centrifuged at 1000× G for 10 minutes at 4° C.; the supernatant was transferred to a new tube and immediately supplemented with 11% supernatant volume of ice-cold 10× Tris-buffered saline (200 mM TrisCl pH 7.5, 1.3 M NaCl). The pellet was resuspended in 1 volume HB Hypotonic Lysis Buffer (10 mM HEPES pH 7.5, 10 mM KCl, 1.5 mM $MgCl_2$), the cells were allowed to swell, and the homogenization and centrifugation steps were repeated. The supernatants were combined and re-centrifuged at 1000× G, 10 minutes, 4° C.

Collecting the Membrane Fraction

The supernatant, from the homogenization step described above, was centrifuged at 2000× G, 10 minutes, 4° C. (Jouan). The pellet was discarded. The supernatant was saved; this is the "2K supernatant". The 2K supernatant was centrifuged at 12,000× G (10,000 rpm (Sorvall SS-34) to collect the membrane fraction (e.g., the pellet includes the membrane fraction). The supernatant was removed and discarded. The pellet was saved; this is the "12K membranes". The 12K membranes were resuspended in 20% glycerol, 20 mM HEPES (1 pellet volume). The membrane fraction was flash frozen in small aliquots and stored at −80° C.

EXAMPLE 3

The following provides a description of the method used for large-scale wash of the membrane fraction. This method was used to prepare membranes that are salt- and alkali-stripped.

Preparing the Washed Membrane Fraction

For all steps of the membrane wash procedure, ice-cold tubes and buffers were used.

The protein concentration of the HeLa cell membrane fraction (e.g., Example 2) was determined using BCA™ Protein Assay Reagent (Pierce, Rockford Ill.), according to manufacturer's instructions. The concentrations ranged from 7–12 mg/ml. An aliquot of membranes, used in multiples of 28 ml, was added to 10 volumes of high EDTA buffer (15 mM EDTA, 50 mM HEPES-pH 7.4, 0.05M KCl, 10% glycerol, 1 mM dithiothreitol, 0.1 mM Pefabloc). The membranes were incubated on ice with intermittent mixing for 15 minutes. The membranes were collected by centrifugation in a SuperLight GSA rotor (SL-1500), 13,000 rpm, 30 minutes, at 4° C. The supernatant was removed. The pellet was resuspended in 10 volumes high salt buffer (50 mM HEPES pH 7.4, 1M NaCl, 10% glycerol, 1 mM EDTA, 1 mM dithiothreitol, 4 µg/ml leupeptin) using a glass rod. The membranes were gently mixed by pipetting up/down and incubating on ice with intermittent mixing for 15 minutes. The membranes were collected by centrifugation as above. The supernatant was removed. The pellet was resuspended in 21 ml No-salt buffer (50 mM HEPES pH 7.4, 10% glycerol, 1 mM EDTA acid, 1 mM dithiothreitol, 4 µg/ml leupeptin) using a glass rod. The next step describes the carbonate wash: twelve volumes (e.g., 252 ml) of ice-cold 0.1M $Na_2CO_{31}$ pH 11.5, was added; the suspension was rocked in a cold room on a nutator for 30 minutes; the suspension was centrifuged as above. The supernatant was removed. The pellet was resuspended in 10 volumes of No-salt buffer using a glass rod, mixed gently, and centrifuged as above. The supernatant was removed. The pellet includes the washed membrane fraction (e.g., the isolated washed membrane fraction), which comprises integral-membrane proteins embedded in the lipid bilayer.

EXAMPLE 4

The following provides a description of the method used to extract the integral-membrane proteins and protein complexes from the washed membrane fraction. The extracted integral-membrane proteins and protein complexes are isolated in detergent-solubilized form.

Preparing the Solubilized Proteins and Protein Complexes

The washed membrane pellet (e.g., Example 3) was resuspended in extraction buffer (20 mM Bis/Tris pH 7.1, 0.5% mCHAPSO detergent solution, 10% glycerol, 1 mM EDTA, 1 mM dithiothreitol, 4 µg/ml leupeptin) at a concentration of 7–8 mg/ml based on the original concentration of protein in the membrane fraction, as determined in Example 3. The resuspended pellet was incubated on ice for 45 minutes with intermittent mixing by slow vortexing, then centrifuged 45 minutes at 50,000 rpm in a Beckman TLA-100.3 rotor at 4° C. to pellet the un-extracted protein and protein complexes. The supernatant was saved, as it includes the integral-membrane proteins extracted from the membrane in detergent-solubilized form. Aliquots of the solubilized integral-membrane proteins were placed into pre-chilled tubes (~10 ml/tube) and quick-frozen in liquid nitrogen, then stored at −80° C. The protein concentration of the soluble preparation was between 0.5–1 mg/ml.

EXAMPLE 5

The following provides a description of the method used for immunoaffinity enrichment of the preparation of solubilized proteins and protein complexes for the gamma-secretase complex.

Immunoaffinity Enrichment of the Gamma-secretase Complexes

The preparation of solubilized integral membrane proteins and protein complexes (e.g., Example 4) was adsorbed onto an anti-PS1 affinity column (e.g., Examples 8 and 9) that was equilibrated with extraction buffer (20 mM Bis/Tris, pH 7.1; 0.5% mCHAPSO detergent solution of 1 part mCHAPSO and 2 parts CHAPSO™; 10% glycerol; 1 mM EDTA; 1 mM dithiothreitol; and 4 µg/ml leupeptin). The adsorption (e.g., binding) was performed at 4° C.

The column was washed with at least 20 column volumes of PBS plus 0.5% CHAPSO™. The column was eluted with 0.1 M glycine, pH 2.5, plus 0.5% CHAPSO™ and 10% glycerol at 4° C. The eluted fractions (1 column volume) were immediately neutralized with 0.15 M Tris/Cl pH 8 (0.1 column volume). The input extract, flow through fraction, and eluted fractions were assayed for gamma-secretase activity using the gel system described in Example 7. None of the input gamma-secretase activity flowed through the antibody column. Typically, 30% of the input activity was recovered in the eluted fraction.

Affinity columns having the anti-PS1 antibody JH2 or JH5-linked matrices partially depleted gamma-secretase activity from a HeLa membrane extract. The combination of these two antibodies completely removed gamma-secretase activity from samples containing the solubilized gamma-secretase complex.

In some experiments, prior to adsorbing the preparation of integral membrane proteins and protein complexes onto a PS1 affinity column, the preparation was loaded onto a Mono S (Pharmacia) cation exchange chromatography, followed by DEAE Sepharose Fast Flow (Pharmacia) anion exchange chromatography, and affinity purified on Wheat Germ Agglutinin agarose. Adsorption of this enriched material was performed in the Wheat Germ Agglutinin (WGA) elution buffer (20 mM Tris/Cl, pH 7.7; 0.5% mCHAPSO detergent solution; 0.1 M NaCl; 30% glycerol; 0.5 M N-acetyl glucosamine; 0.13 mM Pefabloc; and 4 μg/ml leupeptin).

EXAMPLE 6

The following provides descriptions of three different reconstitution methods in which the radiolabeled βAPP polypeptide mimics (e.g., the gamma-secretase substrates) were reacted with: (1) the washed membrane fractions (e.g., Example 3); (2) the solubilized proteins and protein complexes (e.g., Example 4); or (3) the affinity enriched gamma-secretase complex (e.g., Example 5).

A Reconstitution Method Using the Washed Membrane Fractions

The washed membranes (e.g., Example 3) were resuspended in low-salt buffer (50 mM HEPES pH 7.4, 12 μg/ml leupeptin, 0.5 μM o-phenanthroline). 2 μl of the washed membranes were added to 16 μl of gamma-secretase reaction buffer (40% glycerol, 0.5% mCHAPSO detergent solution, 20 mM HEPES pH 7.5) on ice, then 2 μl of solubilized radiolabeled βAPP-C100 (Example 1) were added to make 20 μl final volume of the gamma-secretase reaction mix. Alternatively, 5 μl of washed membranes were added to 13 μl of gamma-secretase cleavage reaction mix on ice, then 2 μl of the solubilized radiolabeled APPC100 polypeptide mimics were added to make a 20 μl final volume of the gamma-secretase reaction mix. The cleavage reaction was initiated by placing the gamma-secretase reaction mix at 37° C. for 20 minutes. The cleavage reaction was terminated by placing the reaction tube on ice. The samples of the cleavage reaction were prepared for SDS-PAGE analysis by addition of 8 μl 4× NuPage Sample Buffer (Novex, San Diego Calif.) and incubation at 95° C. for 5 minutes. The presence of the gamma-secretase cleavage products was detected by performing an SDS-PAGE gel, as described in Example 7 below.

A Reconstitution Method Using the Solubilized Proteins/Complexes

2 μl of solubilized proteins and complexes (Example 4) were added to 16 μl of the gamma-secretase reaction buffer (40% glycerol, 0.5% mCHAPSO detergent solution, 20 mM HEPES pH 7.5) on ice, then 2 μl of solubilized radiolabeled βAPP-C100 polypeptides (Example 1) were added to make a 20 μl final volume of the gamma-secretase reaction mix.

Alternatively, 5 μl of solubilized proteins were added to 13 μl of gamma-secretase cleavage reaction mix on ice, then 2 μl of the solubilized radiolabeled βAPP-C100 polypeptide mimics were added to make a 20 μl final volume of the gamma-secretase reaction mix. The cleavage reaction was initiated by placing the gamma-secretase reaction mix at 37° C. for 20 minutes. The reactions were terminated by placing the gamma-secretase reaction mix on ice, followed by addition of 8 μl 4× SDS-PAGE sample buffer (NOVEX, San Diego, Calif.). Prior to gel electrophoresis, samples were heated to 95° C. for 5 minutes. The presence of the gamma-secretase cleavage products was detected by performing an SDS-PAGE gel, as described in Example 7 below.

A Reconstitution Method Using the Affinity Enriched Gamma-secretase Complex

2 μl of Affinity Enriched Gamma-secretase Complex (Example 5) were added to 16 μl of the gamma-secretase reaction buffer (40% glycerol, 0.5% mCHAPSO detergent solution, 20 mM HEPES pH 7.5) on ice, then 2 l of solubilized radiolabeled βAPPC100 polypeptides (Example 1) were added to make a 20 μl final volume of the gamma-secretase reaction mix.

Alternatively, 5 μl of Affinity Enriched Gamma-Secretase Complex were added to 13 μl of gamma-secretase cleavage reaction mix on ice, then 2 μl of the solubilized radiolabeled βAPP-C100 polypeptide mimics were added to make a 20 μl final volume of the gamma-secretase reaction mix. The cleavage reaction was initiated by placing the gamma-secretase reaction mix at 37° C. for 20 minutes. The reactions were terminated by placing the gamma-secretase reaction mix on ice, followed by addition of 8 μl 4× SDS-PAGE sample buffer (NOVEX, San Diego, Calif.). Prior to gel electrophoresis, samples were heated to 95° C. for 5 minutes. The presence of the gamma-secretase cleavage products was detected by performing an SDS-PAGE gel, as described in Example 7 below.

EXAMPLE 7

The following provides a description of the gel system used to resolve and detect the gamma-secretase cleavage products from the reconstitution methods (e.g., Example 6). The presence of the functionally-active gamma-secretase complexes was detected by monitoring the cleavage of radiolabeled βAPP polypeptide mimics. For example, gamma-secretase cleavage of the 11 kDa βAPP-C100 polypeptide generated the 4 and 6 kDa cleavage products. Similarly, cleavage of the 9 kDa βAPP-C83 polypeptide generated the 3 and 6 kDa cleavage products.

Detection of the Gamma-secretase Cleavage Products

The gamma-secretase cleavage reactions were loaded and run on an SDS-PAGE gel, such as the 10% NuPage™ gels (NOVEX, San Diego, Calif.), according to the manufacturer's directions. Gels were dried and $^{35}$S-labeled βAPP substrate (e.g., apparent 11 kDa βAPP-C100 polypeptide) and cleavage products (e.g., 4 and 6 kDa polypeptides) were detected by phosphorimager analysis (Amersham Pharmacia Biotech, Piscataway, N.J.). The radioactive signals of the radiolabeled substrate and cleavage products were quantitated by phosphorimager.

The radiolabeled βAPP-C100 substrate was cleaved by the gamma-secretase complexes present in the solubilized protein and protein complex preparation (FIGS. 6 and 7) and the affinity enriched protein preparation (FIG. 8), to yield a 6 kDa cleavage product that corresponds to the C-terminal APP polypeptide fragment.

The radiolabeled βAPP-C83 substrate was also cleaved by the gamma-secretase complexes present in the solubilized protein and protein complex preparation (FIG. 7) and the affinity enriched protein preparation, to yield a 6 kDa cleavage product that corresponds to the C-terminal βAPP polypeptide fragment.

EXAMPLE 8

The following provides a description of the methods used to generate the anti-PS1 polyclonal antibodies.

Generating the PS1 Peptide Antigens Using Chemical Synthesis Methods

The anti-PS1 polyclonal antibody, designated 1357, was raised against a synthetic peptide antigen of PS1 having the sequence CRDSHLGPHRSTPESR-amide (SEQ ID NO.:5). This peptide antigen encompasses amino acids 344–358 of PS1, and includes a C-terminal cysteine for coupling the peptide antigen to a carrier protein.

The anti-PS1 polyclonal antibody, designated 1398, was raised against a synthetic peptide of PS1 having the sequence CGHPEPLSNGRPQGNSR-amide (SEQ ID NO.:6). This peptide antigen encompasses amino acids 45–60 of PS1, and includes a C-terminal cysteine for coupling the peptide antigen to a carrier protein.

The anti-PS1 polyclonal antibody, designated SR92, was raised against a synthetic peptide of PS1, having the sequence Norleucine-RDSHLGPHRSTPESR-amide antibody (SEQ ID NO.:9). This peptide encompasses amino acids 344–358 of PS1.

The synthetic peptide antigens used to raise the anti-PS1 polyclonal antibodies 1357, 1398, and SR92, were synthesized by the method of J. Stewart & J. Young, "*Solid phase peptide synthesis*" (Pierce Chemical Company, Rockford, 1984). The 1357 and 1398 polyclonal antibodies were coupled to an ovalbumin carrier protein, via the N-terminal cysteine residues, using m-maleimidobenzoyl-N-hydroxysuccinimide ester as a coupling agent (Harlow, E. and Lane, D. 1988 in: *Antibodies: A Laboratory Manual*, pp 82–83 CSHL, Cold Spring, N.Y.).

Generating the PS1 Peptide Antigens Using Recombinant DNA Technology

The anti-PS1 polyclonal antibody, designated JH2, was raised against a PS1 polypeptide fragment that was expressed in bacteria, using recombinant DNA technology. This polypeptide fragment encompasses amino acids 1–77 of PS1 (SEQ ID NO.: 7). This fragment was generated as a fusion protein with bacterial glutathione-S-transferase using a pGEX4T1 vector (Amersham Pharmacia Biotech, Piscataway, N.J.). PS1 coding sequences (nucleotides 554–786) were amplified from a cDNA library using polymerase chain reaction (U.S. Pat. Nos. 4,683,202 and 4,965,188 (incorporated herein by reference) using primers encoding the terminal EcoR1 and BamH1 sites, and the resulting EcoR1-BamH1 polynucleotide fragment was ligated into pGEX4T1. Growth of bacteria, induction, lysis, purification of inclusion bodies, purification of fusion protein, and cleavage of PS11–77 from GST fusion were performed according to standard protocols provided with GST Purification Module (Amersham Pharmacia Biotech, Piscataway, N.J.).

The anti-PS1 polyclonal antibody, designated JH5, is a purified polyclonal antibody raised against the PS1 "loop"—GST fusion protein (SEQ ID NO.:8). This fusion protein was generated as a fusion protein with bacterial glutathione-S-transferase using a pGEX4T1 vector (Amersham Pharmacia Biotech, Piscataway N.J.). PS1 coding sequences (nucleotides 1382–1769) were amplified from a cDNA library using polymerase chain reaction using primers encoding terminal EcoR1 and BamH1 sites, and the resulting EcoR1-BamH1 polynucleotide fragment was ligated into pGEX4T1. Growth of bacteria, induction, lysis, purification of inclusion bodies and purification of fusion protein were performed according to the protocols provided with GST Purification Module (Amersham Pharmacia Biotech, Piscataway N.J.).

Animal Immunizations for Generating the Polyclonal Antibodies

Rabbits were immunized using approximately 2 mg of peptide-coupled ovalbumin, suspended in 200 μl sterile phosphate-buffered saline which was emulsified together in 200 μl of Freund's complete adjuvant (SIGMA Chemical Company St. Louis, Mo.). The emulsified peptides were injected intradermally at 8–10 sites, as described by Harlow and Lane (in: Antibodies: A Laboratory Manual, 1988, p. 109, CSHL, Cold Spring, N.Y.). An intradermal booster injection containing 100 μg of antigen in 400 μl 50% phosphate-buffered saline/50% Freund's adjuvant (incomplete) was administered three weeks later. A test bleed was conducted two weeks after the booster injection, and for two weeks thereafter while the antibody titer remained high (Harlow and D. Lane, 1988, in: *Antibodies: A Laboratory Manual*, pp. 116–119, CSHL, Cold Spring, N.Y.). The antibody titer was determined by ELISA assay using unconjugated peptide (Harlow and D. Lane, 1988, in: *Antibodies: A Laboratory Manual*, pp. 553–612, CSHL, Cold Spring, N.Y.).

Immunopurification of the Antibodies

These polyclonal antibodies were immunopurified on an antigen column. The antigen column was prepared by binding the appropriate peptide to a Pharmacia HiTrap NHS-activated column (Amersham Pharmacia Biotech, Piscataway, N.J.), according to the manufacturer's instructions. The immunopurification was by a standard method (*Immunoaffinity Purification of Antibodies on an Antigen Column*, pp. 314–5, E. Harlow and D. Lane, "*Antibodies: A Laboratory Manual*" c.1988 CSHL, Cold Spring N.Y.).

EXAMPLE 9

The following provides a description of the method used to isolate a membrane fraction that includes the naturally-occurring, functionally-active gamma-secretase complex (e.g., endogenous gamma-secretase complex) and the substrate (e.g., endogenous substrate). This membrane fraction can be used to screen reagents to identify reagents that inhibit gamma-secretase activity.

Preparation of Membranes that Include the Endogenous Gamma-secretase Complex and Substrate Cellular membranes from HeLa cells, which express a naturally-occurring substrate for gamma-secretase cleavage (e.g., Swedish variant βAPP) as well as endogenous levels of gamma-secretase, were prepared as described in Example 2 above. The protein concentration was determined as described in Example 3, and ranged between 7–12 mg/ml, although dilutions comprising as little as 3 mg/ml of protein were also sufficient to detect gamma-secretase cleavage. The membranes were washed two times in the high salt buffer, as described in Example 3 above. The membranes were not washed with the carbonate solution. Instead, the membranes were washed with a solution containing Tween-80 which preserves the substrate within the membranes. Briefly, the Tween-80 wash is described herein.

The pellet was resuspended in 10 volumes Tween-80 buffer (0.05M HEPES, pH 7.5, 10% glycerol, 0.5% Tween-80) using a glass rod. The suspension was rocked in a cold room on a nutator for 30 minutes. The suspension was centrifuged in a SuperLight GSA rotor (SL-1500), 13,000 rpm, 30 minutes, at 4° C. The supernatant was removed. The pellet was resuspended in 10 volumes of No-salt buffer (50 mM HEPES pH 7.4, 10% glycerol, 1 mM EDTA, 1 mM dithiothreitol, 4 μg/ml leupeptin) using a glass rod, and mixed gently. The suspension was centrifuged as above. The supernatant was removed. The pellet includes the Tween-80 washed membrane fraction, which comprises integral-membrane proteins (e.g., gamma-secretase complex) and the substrate (e.g., βAPP) embedded in the lipid bilayer.

Cleavage of the Endogenous Substrate

Aliquots (5–50 μl) of the Tween-80 washed membranes were suspended in No-salt buffer at a concentration of 0.5–1 mg/ml. The cleavage reaction was initiated by warming the membranes to 37° C. for approximately three hours and the reaction was terminated by placing the samples on ice.

In the protocols for screening inhibitor compounds, the test inhibitor compound was added to the membrane sample at 4–10° C. for a final concentration of approximately 10–30 μM, prior to shifting the temperature to 37° C. Detecting Cleavage by Time-Resolved Fluorescence Cleavage of the endogenous substrate (e.g., βAPP) was detected by quantitative measurement of newly generated cleavage product, such as Aβ peptide. The 9S3.2 antibody (Biosolutions, Newark, Del.) is a high affinity mouse monoclonal antibody that was generated using an Aβ-40 peptide. The 9S3.2 antibody binds specifically to the cleaved C-terminal end of Aβ. This antibody does not bind to precursor (e.g., the βAPP protein). The monoclonal antibody 26D6-B2-B3 is another high affinity mouse monoclonal antibody that was generated using an Aβ 1–12 peptide coupled through the carboxyl terminus to a carrier (SIBIA Neurosciences, La Jolla, Calif.). The 26D6-B2-B3 antibody binds to the N-terminal region of Aβ. It will bind to both precursor and cleavage product.

After termination of the cleavage reaction discussed above, 60 μl of each of the chilled fluorescent-labeled antibodies were added to 20 μl of 1 mg/ml cleaved membranes. 8 replicates of each antibody/membrane combination were assayed. 9S3.2 fluorescent-label antibody was added at 0.3 μg/ml, while 26D6 fluorescent-label antibody was added at 0.8 μg/ml. The fluorescent labeled antibodies were allowed to incubate in the membrane samples at room temperature for 18–24 hours, after which the signal was read by a Discovery® HTRF microplate analyser (Packard Instrument Company, Meriden, Conn.).

Simultaneous binding of 9S3.2 and 26D6-B2-B3 to the cleavage product was detected by modifying these antibodies with an appropriate pair of fluorescent adducts such that fluorescence energy transfer will occur when the adducts are brought in close proximity by binding of the antibodies to Aβ peptide [Kolb], et al., 1996 in: "Homogeneous Fluorescent technology in High Throughput Screening", *Journal of Biomolecular Screening* 1:203–210). The fluorophores were then excited by nitrogen laser pulse and the degree of fluorescence energy transfer was quantitated by time-resolved fluorescence measurements (Kolb, J. M., Yamanaka, G., and Manly, S. P. J. ibid).

Figure 10:
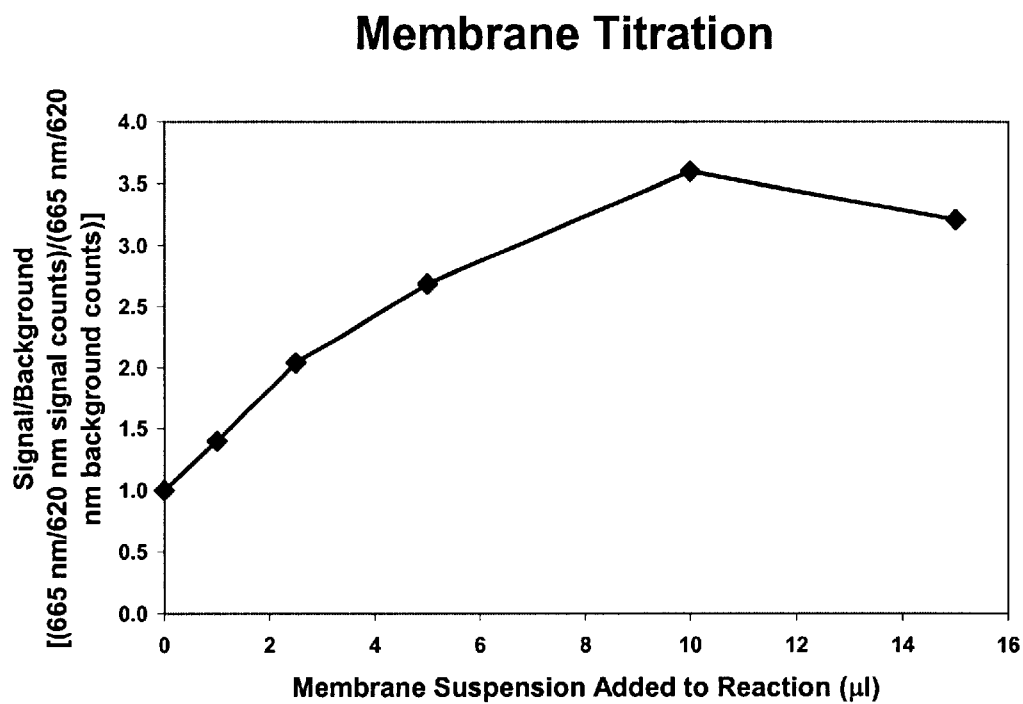
FIG. 10: A graph indicating that increasing volumes of membrane suspension from cells expressing HPLAP-βAPP$^{sw}$ provided a proportionate amount of gamma-secretase activity, as signified by increasing ratios of fluorescent signal/background. The cells were incubated with fluorescent adducts modifying antibodies 26D6 and 9S3.2.

As shown in FIG. 10, the time-resolved fluorescence assay detected gamma-secretase activity in wells having less than 2 μl of membrane suspension of the HPLAP-βAPP$^{sw}$. In addition, the assay was sensitive to increasing amounts of gamma-secretase activity by providing proportionate ratios of fluorescent signal/background.

Figure 11:
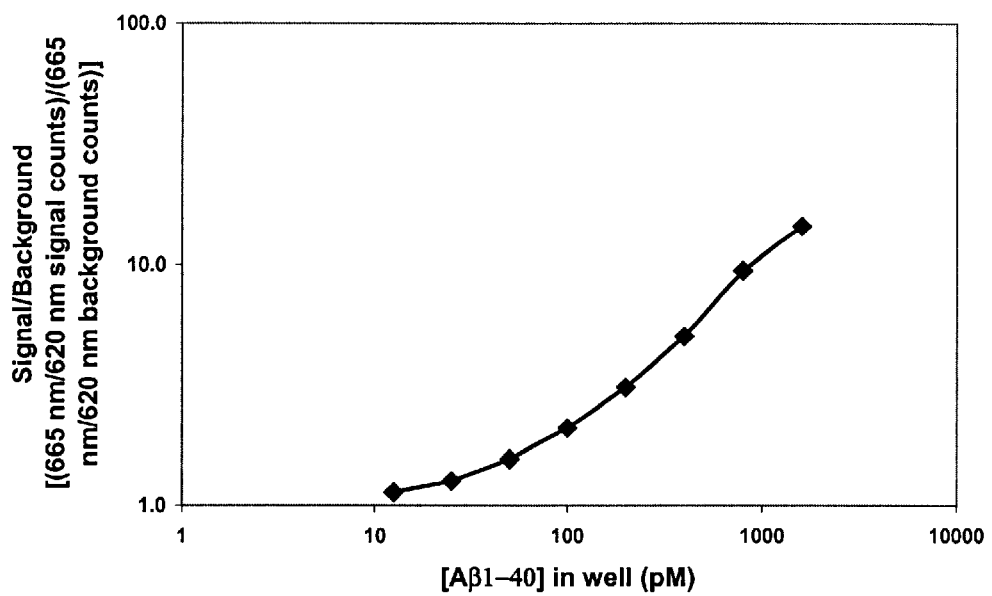
FIG. 11: A graph indicating that increasing concentrations of the Aβ-40 peptide provided a proportionate amount of fluorescent signal. The Aβ peptides were incubated with fluorescent adducts modifying antibodies 26D6 and 9S3.2.

The assay was similarly sensitive in the detection of Aβ fragments, as shown in FIG. 11. Synthetic Aβ-40 peptide was diluted in reaction buffer and incubated with fluorescent adducts modifying antibodies 26D6 and 9S3.2. The fluorescent signal increased in response to increasing concentrations of the Aβ-40 peptide.

What is claimed:

1. An in vitro homogenous method of detecting cleavage of β-amyloid precursor protein (βAPP) by gamma-secretase, said method comprising detecting binding of a gamma-cleaved βAPP fragment with a pair of fluorescent adducts, wherein a first fluorescent adduct binds specifically to the carboxy-terminal end of the gamma-cleaved βAPP fragment with substantially no cross-reactivity to uncleaved βAPP or to other types of gamma-cleaved βAPP fragments, and wherein a second fluorescent adduct binds to the gamma-cleaved βAPP fragment within an amino acid sequence which corresponds to amino acids 1–31 of β-amyloid peptide (Aβ), and wherein excitation of one of the fluorescent adducts provides a detectable transfer of fluorescent energy to the other fluorescent adduct.

2. The method according to claim 1, wherein the method is practiced in a fluid sample in the presence of uncleaved βAPP and other types of gamma-cleaved βAPP fragments.

3. The method according to claim 2, wherein the sample comprises membrane fractions having endogenous gamma-secretase and Swedish variant βAPP.

4. The method according to claim 2, wherein the sample comprises solubilized gamma-secretase complex and βAPP.

5. The method according to claim 1, wherein each of the fluorescent adducts separately modifies an antibody.

6. The method according to claim 5, wherein the gamma-cleaved βAPP fragment is Aβ-40.

7. The method according to claim 6, wherein the first fluorescent adduct modifies a first antibody which binds to Aβ-40 at an epitope comprising amino acid residue 40.

8. The method according to claim 7, wherein the second fluorescent adduct modifies a second antibody which binds to Aβ at an epitope comprising amino acid sequence 1–12.

9. The method according to claim 1, wherein excitation of the first fluorescent adduct provides a detectable transfer of energy to the second fluorescent adduct.

10. The method according to claim 9, wherein the first adduct comprises a molecule selected from the group consisting of lanthanide cryptate or chelate, fluorescein, EDANS, salts of N-[6-amino-9-[2-carboxy-phenyl]-4,5-disulfoxy-3H-xanthen-3-ylidene]aminium ion (2−) and salts of 1-(epsilon-carboxypentyl)-1'-ethyl-3,3,3',3'-tetramethylindocarbocyanine-5,5'-disulfonate ion.

11. The method according to claim 10, wherein the first fluorescent adduct comprises a europium cryptate.

12. The method according to claim 10, wherein the second fluorescent adduct comprises xl-APC.

13. The method according to claim 12, wherein the detectable transfer of energy comprises an amplified signal from the second fluorescent adduct.

14. The method according to claim 1, wherein the other fluorescent adduct comprises a fluorescent quencher molecule.

15. The method according to claim 14, wherein the fluorescent quencher molecule is selected from the group consisting of dabcyl and salts of 9-[2-[[4-carboxy-piperidin-1-yl]sulfonyl]phenyl]-6-(N-methyl-N-phenyl-amino)-3H-xanthen-3-ylidene]-N-methylbenzenaminium ion.

16. The method according to claim 15, wherein each of the fluorescent adducts separately modifies an antibody.

17. The method according to claim 16, wherein the detectable transfer of energy comprises a decrease in fluorescent signal from the fluorescent adduct which is excited.

18. The method according to claims 13 or 17, wherein excitation is by laser, xenon flash lamp or deuterium-tungsten lamp.

19. The method according to claim 18, wherein excitation is by laser.

20. An in vitro homogenous method for determining the presence of β-amyloid peptide (Aβ), in a sample said method comprising:
  (a) exposing the sample to a pair of fluorescent adducts, wherein the first fluorescent adduct binds to the carboxy-terminal region of Aβ and the second fluorescent adduct binds to the amino-terminal region of Aβ and at least one fluorescent adduct is substantially free of cross-reactivity to uncleaved βAPP or to other types of gamma-cleaved βAPP fragments; and
  (b) detecting binding of the pair of fluorescent adducts with Aβ by excitation of one of the fluorescent adducts wherein excitation of one of the fluorescent adducts provides a detectable transfer of fluorescent energy to the other fluorescent adduct.

21. The method according to claim 20, wherein the first fluorescent adduct binds specifically to the carboxy-terminal end of Aβ with substantially no cross-reactivity to uncleaved βAPP or to other types of gamma-cleaved βAPP fragments.

22. The method according to claim 21, wherein Aβ is Aβ-40.

23. The method according to claim 22, wherein each of the fluorescent adducts separately binds specifically to either the amino- and carboxy-terminal ends of Aβ with substantially no cross-reactivity to uncleaved βAPP or to other types of gamma-cleaved βAPP fragments.

24. The method according to claim 21, wherein excitation is by laser, xenon flash lamp or deuterium-tungsten lamp.

25. The method according to claim 24, wherein excitation is by laser.

26. An in vitro homogenous method for determining the presence of β-amyloid peptide Aβ-40 in a sample, said method comprising:
  (a) exposing the sample to a pair of fluorescent adducts; wherein the first fluorescent adduct binds to the carboxy-terminal end of Aβ-40 and the second fluorescent adduct binds to the amino-terminal region of Aβ-40 and the first fluorescent adduct is substantially free of cross-reactivity to uncleaved βAPP or to other types of gamma-cleaved βAPP fragments; and
  (b) detecting binding of the pair of fluorescent adducts with Aβ-40 by excitation of the first fluorescent adduct wherein excitation of one of the fluorescent adducts provides a detectable transfer of fluorescent energy to the other fluorescent adduct.

27. The method according to claim 26, wherein the first fluorescent adduct modifies a first antibody which binds to Aβ-40 at an epitope comprising amino acid residue 40.

28. The method according to claim 27, wherein the first fluorescent adduct modifies a europium cryptate.

29. The method according to claim 28, wherein the second fluorescent adduct modifies a second antibody which binds to Aβ-40 at an epitope comprising amino acid sequence 1–12.

30. The method according to claim 29, wherein the second fluorescent adduct comprises xl-APC.

31. The method according to claim 30, wherein the first fluorescent adduct is excited by laser.

32. An in vitro homogenous method of detecting cleavage of β-amyloid precursor protein (βAPP) by gamma-secretase, said method comprising detecting binding of a 6 kDa C-terminal fragment with a pair of fluorescent adducts, wherein a first fluorescent adduct binds to the amino-terminal end of the 6 kDa C-terminal fragment with substantially no cross-reactivity to uncleaved βAPP or to other types of gamma-cleaved βAPP fragments, and wherein a second fluorescent adduct binds to a portion within the carboxy-terminal region of the 6 kDa C-terminal fragments and wherein excitation of one of the fluorescent adducts provides a detectable transfer of energy to the other fluorescent adduct.

33. The method according to claim 32, wherein each of the fluorescent adducts separately modifies an antibody.

34. The method according to claim 33, wherein one of the fluorescent adducts comprises a molecule selected from the group consisting of lanthanide cryptate or chelate, fluorescein, EDANS, salts of N-[6-amino-9-[2-carboxyphenyl]-4,5-disulfoxy-3H-xanthen-3-ylidene]aminium ion (2−) and salts of 1-(epsilon-carboxypentyl)-1'-ethyl-3,3,3',3'-tetramethylindocarbocyanine-5,5'-disulfonate ion.

35. The method according to claim 34, wherein the other fluorescent adduct comprises a molecule selected from the group consisting of cross-linked allophycocyanins, coumarin, rhodamine, tetramethylrhodamine and salts of 1-(epsilon-carboxypentyl)-1'-ethyl-3,3,3',3'-tetramethylindodicarbocyanine-5,5'-disulfonate ion.

36. The method according to claim 34, wherein the other fluorescent adduct comprises a fluorescent quencher molecule selected from the group consisting of dabcyl and salts of 9-[2-[[4-carboxy-piperidin-1-yl]sulfony-1]phenyl]-6-(N-methyl-N-phenyl-amino)-3H-xanthen-3-ylidene]-N-methylbenzenaminium ion.

37. An in vitro homogenous method of detecting cleavage of β-amyloid precursor protein (βAPP) by gamma-secretase, comprising the steps of:
  (a) binding a first fluorescent adduct to a 6 kDa C-terminal fragment and a second fluorescent adduct to a β-amyloid peptide (Aβ) wherein at least one of the fluorescent adducts has substantially no cross-reactivity to other portions of uncleaved βAPP, and wherein each fluorescent adduct separately comprises either a donor molecule or an acceptor molecule;
  (b) exciting said donor molecule by laser, xenon flash lamps or deuterium-tungsten lamp; and
  (c) detecting a substantially decreased transfer of fluorescent energy to the acceptor molecule.

38. The homogeneous method according to claim 37, wherein the donor molecule is selected from the group consisting of lanthanide cryptate or chelate, fluorescein, EDANS, salts of N-[6-amino-9-[2-carboxy-phenyl]-4,5-disulfoxy-3H-xanthen-3-ylidene]aminium ion (2−) and salts of 1-(epsilon-carboxypentyl)-1'-ethyl-3,3,3',3'-tetramethylindocarbocyanine-5, 5'-disulfonate ion.

39. The method according to claim 38, wherein the acceptor molecule is selected from the group consisting of cross-linked allophycocyanins, coumarin, rhodamine, tetramethylrhodamine and salts of 1-(epsilon-carboxypentyl)-1'-ethyl-3,3,3',3'-tetramethylindodicarbocyanine-5, 5'-disulfonate ion.

40. The method according to claim 39, wherein the step of detecting a substantially decreased transfer of energy comprises detecting no amplified signal from the acceptor molecule or an amplified signal that is substantially less than a signal that is observed when the acceptor molecule is positioned in close proximity to the donor molecule when the donor molecule is emitting.

41. The method according to claim 38, wherein the acceptor molecule is a fluorescent quencher molecule selected from the group consisting of dabcyl and salts of 9-[2-[[4-carboxy-piperidin-1-yl]sulfonyl]phenyl]-6-(N-methyl-N-phenyl-amino)-3H-xanthen-3-ylidene]-N-methylbenzenaminium ion.

42. The method according to claim 41, wherein the step of detecting a substantially decreased transfer of energy comprises detecting an unchanged fluorescent signal from the donor molecule.

43. An in vitro homogenous method of screening for inhibitors of gamma-secretase in β-amyloid precursor protein (βAPP), said method comprising the steps of:
    (a) adding a test compound to a sample comprising gamma-secretase and βAPP;
    (b) adding a pair of fluorescent adducts to the sample, wherein a first fluorescent adduct has binding specificity to the carboxy-terminal end of a gamma-cleaved βAPP fragment with substantially no cross-reactivity to uncleaved βAPP or to other types of gamma-cleaved βAPP fragments, and a second fluorescent adduct has binding specificity to the gamma-cleaved βAPP fragment within an amino acid sequence which corresponding to amino acids 1–31 of β-amyloid peptide (Aβ), and wherein each fluorescent adduct separately comprises either a donor molecule or an acceptor molecule; and
    (c) detecting a substantially decreased transfer of fluorescent energy between the fluorescent adducts after excitation of said donor molecule wherein a substantially decreased transfer of fluorescent energy between said adduct and said donor molecule indicates that said test compound is an inhibitor of gamma-secretase.

44. The method according to claim 43, wherein the donor molecule is selected from the group consisting of lanthanide cryptate or chelate, fluorescein, EDANS, salts of N-[6-amino-9-[2-carboxy-phenyl]-4,5-disulfoxy-3H-xanthen-3-ylidene]aminium ion (2−) and salts of 1-(epsilon-carboxypentyl)-1'-ethyl-3,3,3',3'-tetramethylindocarbocyanine-5, 5'-disulfonate ion.

45. The method according to claim 44, wherein the acceptor molecule is selected from the group consisting of cross-linked allophycocyanins, coumarin, rhodamine, tetramethylrhodamine and salts of 1-(epsilon-carboxypentyl)-1'-ethyl-3,3,3',3'-tetramethylindodicarbocyanine-5,5'-disulfonate ion.

46. The method according to claim 45, wherein the step of detecting a substantially decreased transfer of energy comprises detecting no amplified signal from the acceptor molecule or an amplified signal that is substantially less than a signal that is observed when the acceptor molecule is positioned in close proximity to the donor molecule when the donor molecule is emitting.

47. The method according to claim 44, wherein the acceptor molecule is a fluorescent quencher molecule selected from the group consisting of dabcyl and salts of 9-[2-[[4-carboxy-piperidin-1-yl]sulfonyl]phenyl]-6-(N-methyl-N-phenyl-amino)-3H-xanthen-3-ylidene]-N-methylbenzenaminium ion.

48. The method according to claim 47, wherein the step of detecting a substantially decreased transfer of energy comprises detecting an unchanged fluorescent signal from the donor molecule.

49. An in vitro homogenous method of screening for inhibitors of gamma-secretase in β-amyloid precursor protein (βAPP), said method comprising the steps of:
    (a) adding a test compound to a sample comprising gamma-secretase and βAPP,
    (b) binding a pair of fluorescent adducts to uncleaved βAPP; wherein a first fluorescent adduct binds to a portion within the amino acid sequence of residues 722–770 of uncleaved βAPP, a second fluorescent adduct binds to a portion within the amino acid sequence of residues 671–702 of uncleaved βAPP, and at least one of the fluorescent adducts has substantially no cross-reactivity to other portions of uncleaved βAPP, and wherein each fluorescent adduct separately comprises either a donor molecule or an acceptor molecule; and,
    (c) detecting a transfer of fluorescent energy between the fluorescent adducts after excitation of said donor molecule, wherein a substantially decreased transfer of fluorescent energy between said adduct and said donor molecule indicates that said test compound is an inhibitor of gamma-secretase.

50. The method according to claim 49, wherein the donor molecule is selected from the group consisting of lanthanide cryptate or chelate, fluorescein, EDANS, salts of N-[6-amino-9-[2-carboxy-phenyl]-4,5-disulfoxy-3H-xanthen-3-ylidene]aminium ion (2−) and salts of 1-(epsilon-carboxypentyl)-1'-ethyl-3,3,3',3'-tetramethylindocarbocyanine-5, 5'-disulfonate ion.

51. The method according to claim 50, wherein the acceptor molecule is selected from the group consisting of cross-linked allophycocyanins, coumarin, rhodamine, tetramethylrhodamine and salts of 1-(epsilon-carboxypentyl)-1'-ethyl-3,3,3',3'-tetramethylindodicarbocyanine-5,5'-disulfonate ion.

52. The method according to claim 51, wherein the step of detecting a transfer of energy comprises detecting an amplified signal from the acceptor molecule.

53. The method according to claim 52, wherein the acceptor molecule is a fluorescent quencher molecule selected from the group consisting of dabcyl and salts of 9-[2-[[4-carboxy-piperidin-1-yl]sulfonyl]phenyl]-6-(N-methyl-N-phenyl-amino)-3H-xanthen-3-ylidene]-N-methylbenzenaminium ion.

54. The method according to claim 53, wherein the step of detecting a transfer of energy comprises detecting a decrease of fluorescent signal from the donor molecule.

* * * * *